US007727544B2

(12) United States Patent
Schwartz et al.

(10) Patent No.: US 7,727,544 B2
(45) Date of Patent: Jun. 1, 2010

(54) TREATMENT OF MYOPIA

(75) Inventors: Daniel M. Schwartz, San Francisco, CA (US); Chang Jun Yu, Pasadena, CA (US); Robert H. Grubbs, Pasadena, CA (US); Julia A. Kornfield, Pasadena, CA (US); Scott E. Fraser, Lacanada-flintridge, CA (US); Matthew S. Mattson, Pasadena, CA (US)

(73) Assignees: The Regents of the University of California, Oakland, CA (US); California Institute of Technology, Pasadena, CA (US)

( * ) Notice: Subject to any disclaimer, the term of this patent is extended or adjusted under 35 U.S.C. 154(b) by 1289 days.

(21) Appl. No.: 11/124,673

(22) Filed: May 9, 2005

(65) Prior Publication Data

US 2005/0271590 A1   Dec. 8, 2005

Related U.S. Application Data

(60) Provisional application No. 60/569,137, filed on May 7, 2004.

(51) Int. Cl.
*A61F 2/00* (2006.01)
*A61K 31/74* (2006.01)

(52) U.S. Cl. .................................. 424/427; 424/78.08

(58) Field of Classification Search ........................ None
See application file for complete search history.

(56) References Cited

U.S. PATENT DOCUMENTS

| | | | |
|---|---|---|---|
| 5,310,764 A | 5/1994 | Baranowitz et al. |
| 5,352,310 A | 10/1994 | Natter |
| 5,410,016 A | 4/1995 | Hubbell et al. |
| 5,462,990 A | 10/1995 | Hubbell et al. |
| 5,468,505 A | 11/1995 | Hubbell et al. |
| 5,567,435 A | 10/1996 | Hubbell et al. |
| 5,573,934 A | 11/1996 | Hubbell et al. |
| 5,626,863 A | 5/1997 | Hubbell et al. |
| 5,756,541 A | 5/1998 | Strong et al. |
| 5,798,349 A | 8/1998 | Levy et al. |
| 5,844,016 A | 12/1998 | Sawhney et al. |
| 5,858,746 A | 1/1999 | Hubbell et al. |
| 5,910,510 A | 6/1999 | Strong et al. |
| 5,935,942 A | 8/1999 | Zeimer |
| 5,986,043 A | 11/1999 | Hubbell et al. |
| 6,059,828 A | 5/2000 | Peyman |
| 6,060,582 A | 5/2000 | Hubbell et al. |
| 6,121,341 A | 9/2000 | Sawhney et al. |
| 6,128,525 A | 10/2000 | Zeng et al. |
| 6,140,314 A | 10/2000 | Zeimer |
| 6,149,931 A | 11/2000 | Schwartz et al. |
| 6,153,211 A | 11/2000 | Hubbell et al. |
| 6,225,303 B1 | 5/2001 | Miller et al. |
| 6,248,727 B1 | 6/2001 | Zeimer |
| 6,267,954 B1 | 7/2001 | Abithbol et al. |
| 6,271,233 B1 | 8/2001 | Brazzell et al. |
| 6,306,922 B1 | 10/2001 | Hubbell et al. |
| 6,387,977 B1 | 5/2002 | Sawhney et al. |
| 6,461,640 B1 | 10/2002 | Hubbell et al. |
| 6,465,001 B1 | 10/2002 | Hubbell et al. |
| 6,475,508 B1 | 11/2002 | Schwartz et al. |
| 6,602,975 B2 | 8/2003 | Hubbell et al. |
| 6,632,446 B1 | 10/2003 | Hubbell et al. |
| 6,703,037 B1 | 3/2004 | Hubbell et al. |
| 6,858,229 B1 | 2/2005 | Hubbell et al. |
| 2002/0091229 A1 | 7/2002 | Hubbell et al. |
| 2003/0017501 A1 | 1/2003 | Hageman et al. |
| 2003/0087985 A1 | 5/2003 | Hubbell et al. |
| 2003/0220245 A1 | 11/2003 | Hubbell et al. |
| 2003/0223957 A1* | 12/2003 | Schwartz et al. ......... 424/78.38 |
| 2004/0138329 A1 | 7/2004 | Hubbell et al. |
| 2005/0196427 A1* | 9/2005 | Tirrell et al. ................ 424/427 |

FOREIGN PATENT DOCUMENTS

| | | |
|---|---|---|
| EP | 0995421 | 4/2000 |
| WO | WO 89/09034 | * 10/1989 |
| WO | WO-9731033 | 8/1997 |
| WO | WO-0187560 | 11/2001 |
| WO | WO-0212350 | 2/2002 |
| WO | WO-2004004757 | 1/2004 |

OTHER PUBLICATIONS http://www.webmd.com/eye-health/tc/nearsightedness-myopia-prevention (accessed Oct. 29, 2008).*
English translation of WO 89/09034, Dec. 7, 2009.*
Downs et al., "Viscoelastic Characterization of Peripapillary Sclera: Material Properties by Quadrant in Rabbit and Monkey Eyes," *J. Biomech. Eng.*, 125: 124-131, 2003.
Fisher et al., "Photoinitiated Polymerization of Biomaterials," *Annu. Rev. Mater. Res.*, 31: 171-81, 2001.
Goss et al., *Optometric Clinical Practice Guideline: Care of the Patient with Myopia*, Reference Guide for Clinicians, © American Optometric Association, 1997.
Gottsch et al., "Hematogenous Photosensitization: A Mechanism for the Development of Aferelated Macular Degeneration," *Investigative Ophthalmology & Visual Science*, 31(9): 1674-1682, 1990.
Gottsch et al., "Light-Induced Deposits in Bruch's Membrane of Protoporphyric Mice," *Arch Ophthalmol.*, 111: 126-129, 1993.
Green et al., "Pathologic Features of Senile Macular Degeneration," *Ophthalmology*, 92(5): 615-627, 1985.

(Continued)

*Primary Examiner*—Michael G Hartley
*Assistant Examiner*—Paul Dickinson
(74) *Attorney, Agent, or Firm*—Fulbright & Jaworski LLP

(57) ABSTRACT

The present invention relates to altering the physical and/or chemical properties of at least part of at least one tissue in the eye. In a specific embodiment, it relates to the treatment and/or prevention of myopia. An activating energy source is utilized to photopolymerize or crosslink molecules in the sclera, thereby increasing the strength of the tissue. The individual is administered a crosslinking reagent or photopolymerizable molecule that becomes associated with the membrane, which is then precisely exposed to an energy source, such as light or ultrasound.

10 Claims, 11 Drawing Sheets

OTHER PUBLICATIONS

Haigis et al., "Comparison of immersion ultrasound biometry and partial coherence interferometry for introcular lens calculation according to Haigis," *Graefe's Arch. Clin. Exp. Ophthalmol.*, 238: 765-773, 2000.

Jin et al., "Effect of Electrostatis Interactions between Glycosaminoglycans on the Shear Stiffness of Cartilage: A Molecular Model and Experiments," *Macromolecules*, 34: 8330-8339, 2001.

Kaufman, "Strenthening the Cornea," *Cornea*, 23(5): 432, 2004.

Knapp et al., "Rheology of reconstituted type I collagen gel in confined compression," *J. Rheol.*, 41(5): 971-993, 1997.

Ratner et al., "Biomaterials: Where We have Been and Where We Are Going," *Annu. Rev. Biomed. Eng.*, 6: 41-75, 2004.

Spoerl et al., "Induction of Cross-Links in Corneal Tissue," *Exp. Eye Res.*, 66: 97-103, 1998.

St. Helen et al., "Rheology of the Human Sclera, 1. Anelastic Behavior," *Am. J. Ophthalmol.*, 52: 539-48, 1961.

van Hest et al., "Protein-based materials, toward a new level of structural control," *Chem. Commun.*, 1897-1904, 2001.

Visudyne, "Overview: Verteporfin for Injection," www.visudyne.com, Last accessed Jan. 11, 2010.

Wollensak et al., "Riboflavin/Ultraviolet-A-induced Collagen Crosslinking for the Treatment of Keratoconus," *Am. J. Ophthalmol.*, 135: 620-627, 2003.

Sarker et al., "Tetraorganylborate salts as convenient precursors for photogeneration of tertiary amines", J. Chem. Soc., Perkin Trans., 1998, 2315-2322, No. 2.

Supplementary European Search Report Issued Sep. 10, 2007 re European Application No. EP 05 74 6596.

Wollensak et al., "Collagen crosslinking of human and porcine sclera", J Cataract Refract Surg. Mar. 2004; 689-95; vol. 30(3).

* cited by examiner

Scheme I: Synthesis Rout of Two-photon Polymerization Initiators

Water soluble Two-Photon Polymerization Initiators

A

B

C

D

E

TREATMENT OF MYOPIA

The present invention claims priority to U.S. Provisional Patent Application Ser. No. 60/569,137, filed May 7, 2004, which is incorporated by reference herein in its entirety.

FIELD OF THE INVENTION

The present invention is generally directed to the fields of ophthalmology and cell biology. Specifically, it relates to altering the physical and/or chemical properties of an ocular tissue, such as the sclera. More specifically, it describes treatment for myopia.

BACKGROUND OF THE INVENTION

Myopia affects approximately 25% of the U.S. population, and as high as 80% of the Asian population in some countries. High degrees of myopia (such as >8 diopters, for example) are less common, but are associated with progressive chorioretinal degeneration. In the subset of high myopes who develop this degeneration (pathologic myopia) irreversible visual loss occurs, often during the fifth and sixth decades of life. In Asia, pathologic myopia is the leading cause of untreatable blindness, affecting approximately 1% of the population. At present, there is no proven effective treatment for pathologic myopia.

In degenerative myopia there is progressive axial enlongation of the eye. The excessive axial enlargement in degenerative myopia causes stretching and thinning of the ocular coats (sclera and chorioretinal tissues). Because this stretching and thinning occurs preferentially in the posterior pole and involves the macula, eyes with degenerative myopia are subject to visual loss. The causes of scleral thinning and stretching in degenerative myopia are incompletely understood, but enhanced turnover of scleral collagen and alteration of scleral glycosaminoglycans are contributory in the disease. As the mechanical properties of the sclera are altered in myopia, the eye is prone to stretching due to the load effect of intraocular pressure. Currently, there are no proven means to prevent the excessive ocular enlargement that occurs in degenerative myopia. Were it possible to retard or prevent ocular enlargement, progression of myopia could be diminished and visual loss prevented at least in part. Increasing the tensile strength or modulus of the sclera is a means to prevent ocular enlargement and reduce progression of myopia.

U.S. Pat. No. 5,756,541 is directed to methods to improve visual acuity including administering a photoactive compound in an amount sufficient to localize to a target ocular tissue and irradiating the target tissue with light from a laser, wherein the wavelength of radiation is absorbed by the photoactive compound and the radiation is conducted for a time and at an intensity sufficient to improve visual acuity. In specific embodiments, the photoactive compound is a green porphyrin. U.S. Pat. No. 5,910,510 is directed to an identical method having a particular irradiation timing.

U.S. Pat. No. 5,798,349 regards methods to treat conditions of the eye characterized by unwanted neovasculature, such as AMD, by administering a liposomal formulation of a green porphyrin in an amount and time sufficient to localize in the neovasculature, followed by irradiation of the neovasculature with laser light, wherein the light absorbed by the green porphyrin occludes the neovasculature. In the related U.S. Pat. No. 6,225,303, the irradiance is in a range from about 300 mW/cm$^2$ to about 900 mW/cm$^2$.

U.S. Pat. No. 6,128,525 is directed to method and apparatus controlling dosimetry of photodynamic therapy.

U.S. Pat. No. 5,935,942 regards methods of occluding vasculature in a mammalian eye including co-administering intravenously a fluorescent dye encapsulated with heat-sensitive liposomes and a tissue-reactive agent activated by irradiation. The liposomes are heated in the eye to release their contents, wherein the tissue-reactive agent remains inactive, followed by monitoring of fluorescent dye flow within the vasculature. The tissue-reactive agent is activated in the vasculature having subnormal blood flow, such that the activated agent chemically occludes the vasculature. The related U.S. Pat. No. 6,140,314 methods further comprise co-administration of a tissue-specific factor effective to impair growth or regeneration of a blood vessel. The related U.S. Pat. No. 6,248,727 regards related diagnostic reagents and kits.

SUMMARY OF THE INVENTION

In myopia, there is progressive elongation of the eye and stretching of the ocular tissues. The outermost ocular coat, the sclera, provides mechanical stability to the eye. When the sclera stretches in pathologic myopia, the adjacent retina and choroid are also stretched, and the stretching is disproportionate in the macular region where scleral and retinal thinning is maximal. This leads to formation of a focal out-pouching, or staphyloma. As the macular tissues stretch, retinal cells atrophy, causing irreversible visual loss. Were the progressive stretching of the sclera in the macular region to be arrested, retinal stretching or further retinal stretching would not occur, and vision could be preserved. Efforts have been made to support the macular region with an external donor scleral or synthetic polymer band placed around the eye, but this has never been proven to be effective.

In the present invention, there is provided methods and compositions for treatment and/or prevention of myopia. In particular aspects, the myopia is treated or prevented through strengthening of the sclera, reducing the stretching of the sclera, reducing staphyloma formation, increasing the modulus of the sclera, reducing the compliance of the sclera, and/or reducing the creep in the sclera, for example. In particular, the present inventors fortify scleral tissue, provide greater mechanical stability to the sclera, and/or prevent further reduction of the strength and/or thickness of scleral tissue by altering its chemical and/or physical structure. This can be accomplished in a number of suitable compositions and methods of use thereof in the invention.

In an embodiment of the invention, a crosslinking compound is provided to the sclera to crosslink with compositions already present therein. Individual crosslinking molecules that are directly active (e.g., glyceraldehydes) or are activated using ultraviolet (UV) light (e.g. riboflavin) are known in the art. Toxicological limitations constrain the concentration of the reagent that can be administered. To overcome this limitation, many units of the reagent may be linked into a caged form (for example, a polymer that includes the reagent as a monomer or co-monomer) that is well tolerated by the body. A further limitation known in the art is the toxicity of the UV irradiation. In the present invention, there is uncaging as a method to increase the potency per photon delivered. For example, light is used to cause depolymerization of the caged form to release many reagent molecules from a single light-activation event. Furthermore, the present invention can be used with excitation of the light-activation using either a single photon of adequate energy (e.g., ultra-violet light) or using two or more photons of lower energy (e.g., infrared light) that are absorbed simultaneously to achieve activation of the caged compound.

In one embodiment of the present invention, photocaged reagents are employed to crosslink one or more components of the sclera. The crosslinking agent is rendered effectively bioinert by the caging, and upon irradiation the crosslinking compound is uncaged, thereby rendering the compound suitable for action on a scleral tissue. In particular, the crosslinking reagent is a caged monomer or polymer and following release of the reagent from the cage, active monomers or polymers are generated for crosslinking. A skilled artisan recognizes that this means of delivery by targeted release of the crosslinking agent is particularly suitable for potentially toxic compounds, as the compound does not provide action anywhere besides the intended targeted region, which may also be referred to as the desired region. The crosslinking agent could be an individual compound or a whole chain of molecules, and the photoactivation that releases the crosslinking compound from the cage permits the precision of the activation through irradiation and selective targeting of specific tissues(s). For example, a chain of molecules capped with an end group that is activated using irradiation can depolymerize into a multitude of crosslinking molecules. Such irradiation may be of any suitable form, although in particular the irradiation utilizes light, including by single photon excitation, two-photon excitation, or multi-photon excitation, for example. An alternative embodiment could provide the required energy using ultrasound, for example.

In a specific but exemplary embodiment of photoactivation of a caged crosslinking agent, photocaged reagents, such as coumarin-caged glyceraldehyde (FIG. 1), are employed to crosslink the scleral collagen and/or other scleral proteins upon excitation using two-photon techniques. Because many vital tissues are adjacent to the sclera and it is desirable to limit the chemical modifications to the sclera alone, the agents can be caged so that they are only activated by an appropriate light stimulus, for example two-photon excitation. Specifically, photo-caged glyceraldehyde may be caged with coumarin that has a high two-photon absorbance cross-section. The caged (inactive molecule) is administered in any suitable manner, such as by retrobulbar injection. This causes the caged agent to diffuse broadly into the sclera and orbital tissues. The caged agent is then selectively activated using irradiation, such as two photon excitation, to uncage it in scleral tissue, causing scleral stiffening. The inactivated caged agent diffuses into the bloodstream and is excreted.

In another embodiment, a macromer is provided to the sclera to form a network within and/or around the sclera, such as a network that interpenetrates the compositions of the sclera. A macromer is a molecule that comprises a number of monomer units (for example, ethyleneglycol, amino acid or saccharide units, for example) and two or more reactive moieties capable of forming covalent linkages to each other (such as acrylate, methacrylate or vinyl groups, for example). It is known in the art to apply a monomer or macromer in a liquid form to the surface of a tissue (for example, the lumen of a blood vessel) or into a void (for example, an empty lens capsule or a crack in a bone) followed by polymerization in situ. The spatial extent of the polymerization is governed in large part by the surface or void to which the monomer or macromer is applied. In the present invention, an existing tissue is permeated by a macromer and the polymerization is performed within the tissue. In particular, a photopolymerizable macromer or mixture thereof having one or more pendant groups that can be linked to each other, to components of the scleral tissue, or to both, is provided in conjunction with a photoinitiator to the sclera. Light is applied to the desired tissue having the photopolymerizable compound, or mixture of compounds, and photoinitiator, thereby resulting in polymerization of the pendant groups to each other, to molecules in the sclera, or to both. In specific embodiments, a mixture of a macromonomer suited for photopolymerization and a photoinitiator are delivered to the eye. Irradiation, such as by single photon excitation, two photon excitation, or multi-photon excitation, for example, is applied to the targeted tissue, thereby resulting in strengthening of the tissue. The photopolymerizable macromer may be any suitable compound so long as it is polymerizable upon exposure to light and/or in the presence of a photoinitiator. In particular embodiments, the photopolymerizable compound comprises polymerizable end groups, such as acrylate, diacrylate, triacrylate, methacrylate, dimethacrylate, trimethacrylate, and vinyl, and an oligomer that confers solubility in water and that is well tolerated by ocular tissues, such as oligoethyleneglycol (PEG). In particular, polyethylene glycol (PEG), PEG-copolymers, poly(amino acids), poly(amino acid)-copolymers, proteins, polycarbohydrates, PEG-based compounds, hydrogels, and so forth may be employed as the photopolymerizable compound.

In a specific embodiment concerning photopolymerizable compounds, there is photo-initiated polymerization inside scleral tissue utilizing a mixture of macromonomer, such as poly(ethylene glycol) dimethacrylate (PEGDM) (FIG. 2), and a photoinitiator, such as that provided in FIG. 3, for example. The reagents may be administered in any suitable manner, such as by retrobulbar injection. The exemplary two-photon excitation is precisely controlled to initiate the polymerization of the macromer in the sclera, which will fortify the scleral tissue.

The utilization of a photoinitiator with a photopolymerizable compound is beneficial. A skilled artisan recognizes that the choice of photoinitiator dictates the type of light source employed, and that different photoinitiators are active at different wavelengths and with different efficiencies. In particular, the spatial resolution with which the photoinitiator can be excited is dependent on whether the photoinitiator is excited via single-photon or multi-photon excitation. The photoinitiators may be water soluble, inhibited by oxygen, and are preferably biocompatible. Diffusion of the photoinitiators into the sclera is governed by the size of the compounds, and the hydrophilic and/or hydrophobic interactions of the photoinitiators with the sclera. Desired diffusion rates will be fast in order to minimize treatment time, and will preferably match diffusion rates of the photopolymerizable compound. High efficiency photoinitiators are desirable because irradiation energy, irradiation time, and photoinitiator concentration is minimized. Preferably, oxygen acts as an inhibitor to lower the efficiency of the photoinitiator and effectively reduce the polymerization. This inhibition will provide a method of protecting oxygen carrying blood vessels from deleterious effects of polymerization. In specific embodiments, photoinitiators are employed that are water soluble, non-toxic, and sensitive to the amount of oxygen concentration. Oxygen sensitivity may be exploited to protect the vasculature in and near the sclera.

Although in particular embodiments, light is employed, the suitable methods to photopolymerize, including to uncage an agent, may be further defined as single photon excitation, two photon excitation, and multi-photon excitation. In particular aspects of the invention, imaging is used, for example optical coherence tomography (OCT)-Doppler technology, is employed, such as to characterize and target scleral tissue for irradiation and treatment (such as is described in U.S. patent application Ser. No. 10/611,013, which is incorporated by reference herein in its entirety), for example. In an additional specific embodiment, light energy comes from any focused light source, including a laser source, for example. For single photon excitation, a skilled artisan recognizes that the light does not have to be focused and that a broad beam of light irradiating the tissue is sufficient. In an additional specific embodiment, regions selected for treatment are illuminated with light in a programmed pattern, by one of a number of techniques familiar to those skilled artisans, including, but not limited to programmed galvanometers or DLP micromirror arrays, for example. The treatment irradiation is of a suitable intensity and wavelength sufficient for its desired activity, including for uncaging a crosslinking reagent or for triggering polymerization of a photopolymerizable compound. In another specific embodiment, light energy comes from a focused laser source, and the treatment area is controlled by one of a variety of techniques including, but not limited to, galvanometer steering optics.

OCT may be utilized for detection in the targeted tissues, such as detection of changes in the composition (such as scattering or labeling with a specific agent) or the organization of the sclera. Doppler OCT provides diagnostic information, such as that regarding mobility, position, and/or depth of the scatterers in the sclera and/or targeting of the particular region of interest for diagnosis and/or treatment by the activation and uncaging of the crosslinking reagent or polymerization of the photopolymerizable compound.

In specific embodiments, the invention is provided to a mammal, such as a human in need of treatment or prevention of myopia. The individual may be an individual known to have myopia or be susceptible to myopia, or it may be to an individual suspected of developing myopia. The present invention may also be used to arrest progression of low and moderate myopia. In specific embodiments, the same therapy could be adopted to minimize changes with lower degrees of myopia and prevent the need for spectacle correction. In lower levels of myopia, there is also axial elongation of the globe, but it is less marked than in pathologic myopia.

The scleral stiffness may be characterized in patients with suspected or confirmed pathologic myopia. Myopia may also be determined through identification of abnormal axial length (such as determined by ultrasound or partial coherence interferometry, for example) and refractive error. In embodiments wherein these measurements were abnormal, and further may be associated with early scleral thinning, the compositions of the present invention could be administered as described and subjected to light to cause scleral strengthening. Periodically, the patient may be re-evaluated by determination of scleral thickness and/or stiffness. If abnormal changes were detected, the scleral strengthening procedure could be repeated. This method would prevent or minimize scleral stretching and preserve vision in those affected by pathologic myopia.

In particular aspects, compositions of the invention are biocompatible and/or non-toxic. Also, one of skill in the art recognizes that photoactivation employed in the context of the invention does not damage or deleteriously affect the eye and eyesight.

In particular aspects of the invention, the methods and compositions of the invention strengthen a targeted tissue, such as a sclera of an eye. In specific embodiments, particular tissues of the eye are not targeted, such as those in which hardening would be deleterious. For example, the present invention is particularly well-suited to avoid hardening of blood vessel walls in the eye, and particularly those within or adjacent to the sclera. That is, in particular embodiments the present invention employs selective polymerization in the sclera, and in doing so avoids blood vessels due to higher oxygen content around them, which inhibits photopolymerization.

In another specific embodiment of the present invention, a molecule of the invention is administered to the individual in a pharmacologically acceptable composition. In another specific embodiment, the molecule is administered in a pharmacologically acceptable composition systemically and/or locally to the individual. In an additional specific embodiment, the molecule is administered in a pharmacologically acceptable composition to the individual in any suitable manner, such as orally; by injection, such as retrobulbar injection, periocular injection, intraocular injection, or intravenous injection; or topically, for example.

In a further specific embodiment, the energy utilized in the present invention is light, although in an alternative embodiment the energy is ultrasound, for example.

In another embodiment of the present invention, there is a method of treating myopia in at least one eye of an individual, said myopia characterized by a stretched sclera or weakened sclera, comprising administering to the individual a molecule in an amount sufficient for the molecule to associate with the sclera; and exposing the sclera to an activating source, wherein following the exposing step, the mechanical stability of the eye improves. Improved mechanical stability may be associated with one or more of the following: for example, the sclera thickens, the thinning of the sclera is reduced or halted, the schleral modulus is increased, the compliance is reduced, the creep is reduced, and so forth. In an additional specific embodiment, the molecule is administered in a pharmacologically acceptable composition.

In an additional embodiment of the present invention, there is a kit, housed in a suitable container, comprising a composition of the present invention, such as a caged crosslinking reagent, a photopolymerizable compound, a photoinitiator, or a mixture thereof. In a specific embodiment, the kit further comprises an activating source for activation of said inactive agent. The kit may be further defined as a kit for treating and/or preventing myopia, reducing scleral stretching, retarding scleral stretching, increasing the modulus of the sclera, decreasing compliance of the sclera, reducing creep of the sclera, and so forth.

In another embodiment of the present invention, there is a method of diagnosing an eye disorder in at least one eye of an individual, based on the intrinsic light scattering from targeted tissue, such as the sclera. The technique of optical coherence tomography (OCT) with visible or infrared light is used to detect alterations in the physical and/or chemical nature of the sclera in the eye. OCT can be used to see not only the structure in the eye as has been used in some previous work on the human eye, but can also be used to study the mobility of the structures and the chemical nature of the tissue. In this embodiment, OCT and/or its variants are used to determine the nature of the sclera with or without altered properties to permit guided treatment.

A skilled artisan recognizes that diagnosing axial enlargement in degenerative myopia is routine and may be accomplished by standard means, which in particular aspects includes ultrasound, partial coherence interferomety, but also OCT and OCT Doppler, for example.

In one embodiment of the present invention, there is a method for altering the sclera in an individual, comprising the steps of administering to the sclera a molecule in an amount sufficient to allow the molecule to accumulate in the sclera; and exposing the molecule to an activating source, wherein the activating source activates the caged molecule into an active form or photopolymerizes the molecule, the activation resulting in alteration of at least part of the sclera.

In an embodiment of the present invention, there is a method of treating and/or preventing myopia in an individual, comprising the step of providing to the sclera of the individual a crosslinking compound comprised with a photoactivatable caging agent, wherein upon photoactivation of the caging agent the crosslinking compound crosslinks at least one molecule of the sclera. In specific embodiments, the crosslinking compound is further defined as a single crosslinking molecule, as a chain of crosslinking molecules, or a mixture thereof. In an additional specific embodiment, the molecule of the sclera is a protein polysaccharide, glycosaminoglycan, proteoglycan, or combination or mixture thereof. In further specific embodiments, the protein is collagen and/or the crosslinking compound comprises glyceraldehyde. In additional embodiments, the photoactivation comprises single photon excitation, two photon excitation, or multi-photon excitation. Specific caging agents may comprise an o-nitrobenzyl group, desyl group, phenacyl group, trans-o-cinnamoyl group, coumarinyl group, quinoline-2-onyl group, xanthenyl group, thioxanthenyl group, selenoxanthenyl group, anthracenyl group, or stilbenyl group.

In an additional embodiment of the present invention, there is a method of treating and/or preventing myopia in an individual, comprising the step of providing to the sclera of the individual: a photopolymerizable compound having at least one end group suitable for polymerization; and a photoinitiator, wherein upon exposure to light the compound polymerizes with itself, with a molecule of the sclera, or both. In particular embodiments, the end group of the photopolymerizable compound is further defined as comprising an acrylate, diacrylate, triacrylate, methacrylate, dimethacrylate, trimethacrylate, and/or vinyl end group. In another specific embodiment, the photopolymerizable compound is further defined as PEG-based, such as poly(ethylene-glycol) dimethacrylate (PEGDM), for example, or a hydrogel, for example.

The exposure to light may be further defined as single photon excitation, two photon excitation, or multi-photon excitation. In a specific embodiment, the photoinitiator is water soluble. The photoinitiator is inhibited by oxygen, in additional specific embodiments.

In an additional embodiment of the present invention, there is a method of treating and/or preventing myopia in an individual, comprising the steps of providing to the sclera of the individual a crosslinking compound caged with a photoactivatable caging agent; photoactivating the photoactivatable caging agent; and crosslinking at least one molecule of the sclera.

In another embodiment of the present invention, there is a method of altering one or more mechanical properties of an ocular tissue comprising one or both of the following: 1) providing to the ocular tissue of the individual a crosslinking compound comprised with a photoactivatable caging agent, wherein upon selective photoactivation of the caging agent the crosslinking compound crosslinks at least one molecule of the ocular tissue; and 2) providing to the ocular tissue of the individual: a photopolymerizable compound having at least one end group suitable for polymerization; and a photoinitiator, wherein upon exposure to light the compound polymerizes with itself, with a molecule of the ocular tissue, or both. In specific embodiments, the ocular tissue comprises at least part of a cornea, sclera, eyelid, iris, trabecular meshwork, or outflow channel. In another specific embodiment, the crosslinking agent is further defined as crosslinking itself to a compound in the ocular tissue. In particular embodiments, the crosslinking agent does not facilitate crosslinking between two or more components already present in the ocular tissue but itself is one of the one or more molecules being crosslinked.

In an embodiment of the present invention, there is a method of treating and/or preventing myopia in an individual, comprising the step of providing to the sclera of the individual a crosslinking compound comprised with a photoactivatable caging agent, wherein upon photoactivation of the caging agent the crosslinking compound crosslinks at least one molecule of the sclera. The crosslinking compound may be further defined as a single crosslinking molecule or as a chain of crosslinking molecules. The molecule of the sclera may be any molecule comprised at least in part therein, and in specific embodiments is a protein, polysaccharide, carbohydrate, glycosaminoglycan, proteoglycan, or combination thereof. In a specific embodiment, the protein is collagen. In an additional specific embodiment, the crosslinking compound comprises glyceraldehyde. In another specific embodiment, the photoactivation comprises single photon absorbance, two photon absorbance, or multi-photon absorbance. In a further specific embodiment, the caging agent comprises an o-nitrobenzyl group, desyl group, phenacyl group, trans-o-cinnamoyl group, coumarinyl group, quinoline-2-only group, xanthenyl group, thioxanthenyl group, selenoxanthenyl group, anthracenyl group, or stilbenyl group.

In another embodiment, there is a method of treating and/or preventing myopia in an individual, comprising the step of providing to the sclera of the individual: a photopolymerizable compound having at least one end group suitable for polymerization; and a photoinitiator, wherein upon exposure to light the compound polymerizes with itself, with a molecule of the sclera, or both. In a specific embodiment, the end group of the photopolymerizable compound is further defined as comprising an acrylate, diacrylate, triacrylate, methacrylate, dimethacrylate, trimethacrylate, or vinyl group. In another specific embodiment, the photopolymerizable compound is further defined as PEG-based, such as poly(ethylene-glycol)dimethacrylate (PEGDM), or a hydrogel. In another specific embodiment, the photoactivation comprises single photon absorbance, two photon absorbance, or multi-photon absorbance. The photoinitiator may be water soluble and/or inhibited by oxygen, for example.

In a specific embodiment of the present invention, there is a photopolymerizable compound that comprises a polypeptide, such as elastin, for example, which may be further defined as native elastin or an engineered elastin. In further specific embodiments, the polypeptide is further defined as having one or more natural amino acid substitutions suitable for polymerization and/or wherein the polypeptide is further defined as having one or more non-natural amino acids comprising one or more chemical groups that are appropriate for polymerization, for photoinitiation, or both.

In an additional embodiment of the present invention, there is a method of treating and/or preventing myopia in an individual, comprising the steps of: providing to the sclera of the individual a crosslinking compound caged with a photoactivatable caging agent; photoactivating the photoactivatable caging agent; and crosslinking at least one molecule of the sclera.

In another embodiment of the present invention, there is a method of altering one or more mechanical properties of an ocular tissue comprising one or both of the following: 1) providing to the ocular tissue of the individual a crosslinking compound comprised with a photoactivatable caging agent, wherein upon selective photoactivation of the caging agent the crosslinking compound crosslinks at least one molecule of the ocular tissue; and 2) providing to the ocular tissue of the individual: a photopolymerizable compound having at least one end group suitable for polymerization; and a photoinitiator, wherein upon exposure to light the compound polymerizes with itself, with a molecule of the ocular tissue, or both. In specific embodiments, the ocular tissue comprises at least part of a cornea, sclera, eyelid, iris, trabecular meshwork, or outflow channel. In further specific embodiments, the crosslinking agent is further defined as crosslinking itself to a compound in the ocular tissue.

In an additional embodiment of the present invention, there is a method of treating and/or preventing myopia in an individual, comprising the step of providing to the sclera of the individual a crosslinking compound comprised with a photo-activatable caging agent, such that the compound may be specifically activated by irradiation to produce crosslinks in a desired region of the tissue. In a specific embodiment, the crosslinking compound yields a single crosslinking molecule when it is activated. In another specific embodiment, the crosslinking compound yields two or more crosslinking molecules when it is activated. In a further specific embodiment, the crosslinking compound comprises a plurality of repeat units that become individual crosslinking molecules upon activation. In an additional specific embodiment, the crosslinking reaction is capable of forming a bond with a molecule of the sclera.

In another embodiment of the present invention, there is a method of treating and/or preventing myopia in an individual, comprising the step of providing to the sclera of the individual: a photopolymerizable compound having at least one moiety suitable for polymerization; and a photoinitiator, wherein upon exposure to light the compound is capable of forming a covalent bond with another molecule of the compound, with a molecule of the sclera, or with both. In a specific embodiment, the moiety of the photopolymerizable compound is further defined as comprising an acrylate, diacrylate, triacrylate, methacrylate, dimethacrylate, trimethacrylate, or vinyl group. In a further embodiment, the photopolymerizable compound is further defined as a hydrophilic polymer, which may comprise polyethyleneglycol (PEG), a protein, or a polysaccharide. In a specific embodiment, the polysaccharide comprises poly(hyaluronic acid), dermatansulfate, chondroitinsulfate or keratansulfate, for example.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE FIGURES

For a more complete understanding of the present invention, reference is now made to the following descriptions taken in conjunction with the accompanying drawings.

DESCRIPTION OF ILLUSTRATIVE EMBODIMENTS

Figure 1:
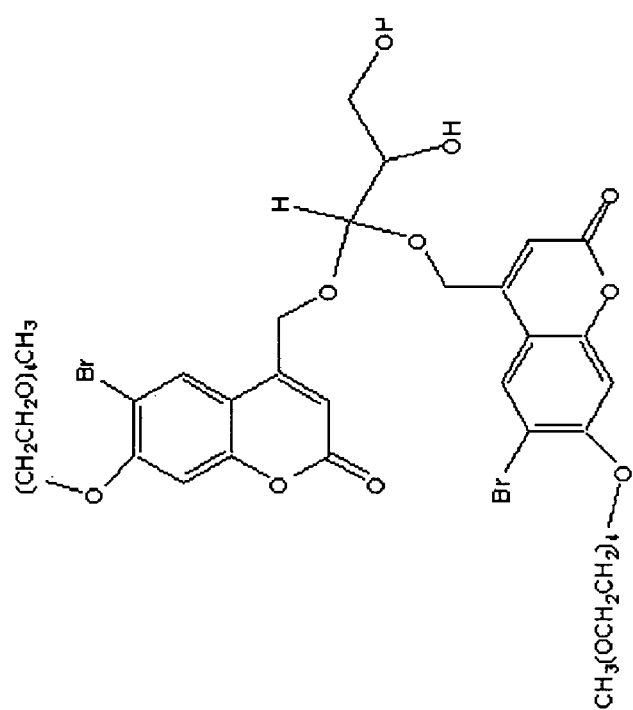
FIG. 1 illustrates an exemplary embodiment of a photocaged reagent of the present invention.
Figure 2:
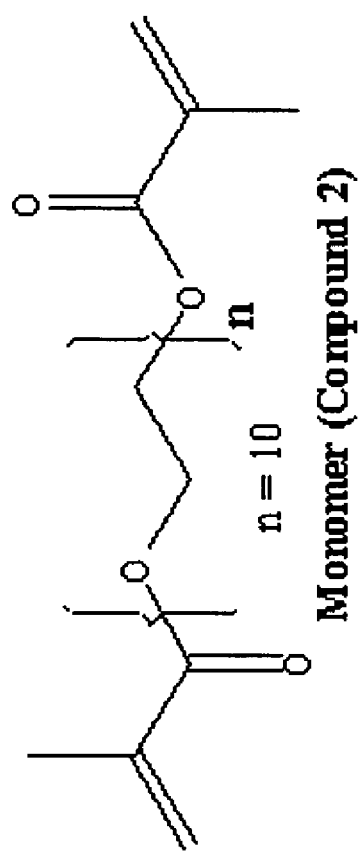
FIG. 2 illustrates an exemplary embodiment of a monomer for mixture with a photo initiator.
Figure 3:
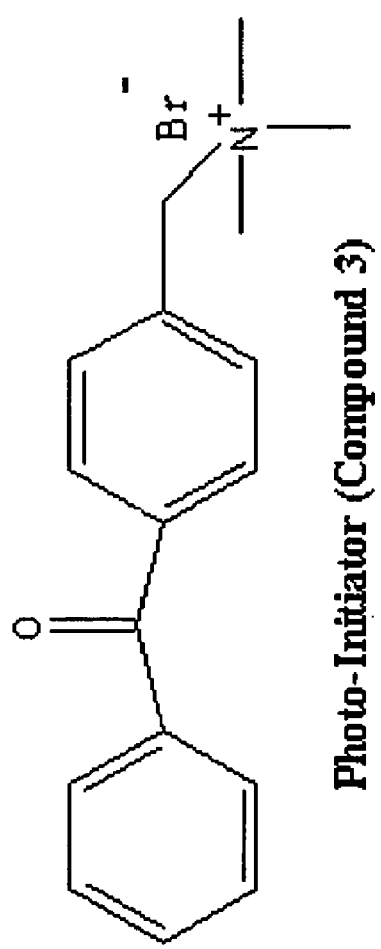
FIG. 3 illustrates an exemplary embodiment of a photoinitiator of the present invention.

It will be readily apparent to one skilled in the art that various substitutions and modifications may be made in the invention disclosed herein without departing from the scope and spirit of the invention. A skilled artisan recognizes that in some embodiments the invention consists essentially of one or more elements of the invention and/or a method of the invention consists essentially of one or more steps of the invention or employs one or more elements of the invention.

I. Definitions

As used herein the specification, "a" or "an" may mean one or more. As used herein in the claim(s), when used in conjunction with the word "comprising", the words "a" or "an" may mean one or more than one. As used herein "another" may mean at least a second or more.

The term "biocompatible" as used herein refers to a compound that is not toxic or injurious to an individual. However, although a compound may be considered toxic, it may nevertheless be employed in the present invention if protected, such as by a caging agent, for example. The toxic compound would not be released except under targeted, specific activation of the caging agent, such as with light directed upon the desired specific tissue having the caged compound.

The term "caged" as used herein refers to the functional groups of a tissue-altering molecule being protected by another molecule/moiety. In a specific embodiment, the term refers to maintaining an inactive form of the tissue-alternating molecule until activated by an energy source.

The term "compliance" as used herein refers to the numerical value of the measured deformation of a material divided by stress of the material.

The term "creep" as used herein refers to the continual gradual deformation of a material under stress. In particular, the material comprises at least part of the sclera.

The term "mechanical stability" as used herein refers to the ability of a tissue or organ to maintain its functional shape even under the influence of stresses imposed on it in the body.

The term "modulus" as used herein refers to a constant or coefficient that represents, such as numerically, for example, the degree to which a substance or body possesses a mechanical property (such as strength or elasticity, for example). A skilled artisan recognizes that the ranges of modulus depend on the exact method of measurement, the specific type of modulus being measured, the material being measured, and in the case of the sclera, the condition of the tissue (as in age or health) and the tissue's location on the ocular globe.

The term "multi-photon excitation" as used herein refers to the application of light that may activate a molecule through the near simultaneous absorption of more than one photon. This may be also stated as referring to the excitation of an atom or molecule by means of absorption or scattering of several photons simultaneously or near simultaneously. In a specific embodiment, the multi-photon excitation is of suitable intensity and wavelength to cause an absorbing compound to reach an activated state, that is to uncage a caged molecule or to polymerize a photopolymerizable compound. Such multi-photon absorbance can take place by different processes, including those in which the photons activate the absorbing material through near simultaneous absorbance, and those in which the multiple photons are absorbed sequentially.

The term "myopia" as used herein, which may also be referred to as near-sightedness, refers to the ability to clearly see objects up close but not those at a distance. The present invention is suitable for all forms and degrees of myopia. In specific embodiments, myopia is pathologic and is diagnosed when eyeball elongation is associated with thinning of ocular tissues in the posterior portion of the globe. High myopia is defined as greater than 8 diopters.

The term "poly(ethylene-glycol) (PEG)-based compound" as used herein refers to a compound comprising more than one partial or whole poly(ethylene-glycol) backbone monomer of ethylene-glycol with or without differing endgroups and also comprising some or no other monomers such as, for example, dimethyl siloxane, methyl methacrylate, lysine, arginine, chondroitin sulfate, keratin sulfate, etc. In specific embodiments, it is defined as an oligomer or a polymer comprising the repeated units of ethylene glycol (—$OCH_2CH_2$—).

The term "photopolymerizable" as used herein refers to the ability of the material to be activated by light and in turn react with themselves or other molecules to form chains, branches, or other conformations through covalent bonds. In specific embodiments, the photopolymerization comprises polymerization with another photopolymerizable molecule or subunit thereof, polymerization with a molecule of the sclera, or both. In particular aspects, the term refers to at least one molecule that changes the physical, chemical, or both properties of a tissue such that a tissue modulus is increased and/or such that the strength of a tissue is increased (or that a reduction in strength is prevented or retarded). In particular aspects of the invention, it is a compound that is able to form an oligomer or a polymer under the irradiation of light with and without initiators.

The term "prevention of myopia" as used herein refers to the avoidance of the development of myopia. Although in specific embodiments the myopia is permanently avoided, in alternative embodiments the onset of myopia is delayed. In further specific embodiments, the individual in which myopia is prevented is an individual susceptible to developing myopia.

The term "sclera" as used herein refers to the outer fibrous coat of the eye, continuous with cornea anterioly and the optic nerve posteriorly.

The term "single photon excitation" as used herein refers to the application of light that may activate a molecule through the absorption of a single photon This may also be stated as the excitation of an atom or molecule by means of absorbing or scattering of a single photon. In a specific embodiment, the single photon excitation is of suitable intensity and wavelength to uncage a caged molecule or to polymerize a photopolymerizable compound.

The term "treatment of myopia" as used herein refers to the amelioration of at least one symptom of myopia or refers to the retarding of the scleral stretching, retarding of scleral thinning, or retarding the reducing of scleral strength, for example. Furthermore, a skilled artisan recognizes that the treatment does not need to improve vision, such as improving it to its fullest extent. In particular aspects, the term refers to preventing the progression or slowing the progression of myopia, such as degenerative myopia, for example. In a specific embodiment, the vision stabilizes.

The term "two photon excitation" as used herein refers to the application of light which may activate a molecule through the near simultaneous absorption of two photons. Stated in another way, it refers to excitation of an atom or molecule by means of absorption or scattering of two photons simultaneously or in close temporal proximity. In a specific embodiment, the two photon excitation is of suitable intensity and wavelength to uncage a caged molecule or to polymerize a photopolymerizable compound. In a specific embodiment, the two photon irradiation is of suitable intensity and wavelength to cause an absorbing compound to reach an activated state, that is, to uncage a caged molecule or to polymerize a photopolymerizable compound. Such two photon absorbance can take place by different processes, including those in which the photons activate the absorbing material though simultaneous or near-simultaneous absorbance, and those in which the two photons are absorbed sequentially.

II. The Present Invention

The present invention is directed to the treatment and/or prevention of myopia, particularly by affecting the physical and/or chemical nature of the sclera. In specific embodiments, the sclera is stretched in myopia, and particularly in pathologic myopia, and the present invention alleviates this stretching or reduces continued stretching at least partially, which thereby imparts greater strength to the sclera or impedes losing any additional strength of the sclera. In a specific embodiment, the methods and compositions affect the sclera to arrest or slow progression of myopia.

Generally, an individual with signs or symptoms of myopia or susceptible to developing myopia is administered, such as systemically or locally, at least one of the two following compounds: 1) a crosslinking reagent caged by a photoactivatable caging agent; and/or 2) a photopolymerizable compound that is activated selectively with light. In particular, there is use of the compounds such that the modulus of the sclera is increased and/or such that the sclera does not stretch any further. In either case, a targeted light source is applied to the sclera or one or more regions thereof. In specific embodiments, following sufficient time for adequate distribution of the photopolymerizable agents, the molecules accumulate within multiple tissues, including the sclera. Given that the sclera is precisely targeted with an energy source, such as light or alternatively ultrasound, the uncaging of the crosslinking reagents occurs selectively and the photopolymerizable molecules are activated selectively or preferentially within the sclera.

III. Myopia

In specific embodiments of the invention, myopia, which may also be referred to as nearsightedness, occurs when light entering the eye focuses in front of the retina instead of directly on it. This is caused by a cornea that is steeper and/or an eye that is longer than a normal eye. Nearsighted people typically see well up close, but have difficulty seeing far away. Myopia often manifests in children, usually becomes progressively worse through adolescence, and stabilizes in early adulthood; symptoms may include blurry distance vision and/or vision that seems clearer upon squinting.

Nearsightedness usually is a mildly debilitating condition that is easily correctible, in most instances with glasses, contacts or refractive surgery. In specific embodiments, the present invention regards, but is limited by, those cases where the myopia is so severe it is considered pathologic (about two percent of Americans are afflicted). Pathologic myopia, which may also be referred to as degenerative myopia, typically begins developing by the second decade of life. The stretching of the eyeball may worsen with age, in some embodiments, resulting in a progressive and severe loss of vision ordinarily during the fifth to seventh decades of life. In specific embodiments, there is also an abnormal growth of new blood vessels (neovascularization) beneath the macula.

The degree of myopia is determined by measurement of refractive error in diopters, axial length determination, and clinical exam of the posterior retina and optic nerve. One of skill in the art is aware of references pursuant to the different classifications of myopia, such as is reviewed in Goss et al., "Optometric Clinical Practice Guideline Care of the Patient with Myopia," American Optometric Association, 1997.

IV. Crosslinking Embodiments

In particular aspects of the invention, a crosslinking reagent is provided to a sclera to crosslink one or more molecules in the sclera, thereby providing strength to the sclera. In specific embodiments, the crosslinking reagent may be more toxic to some tissues and less toxic or not toxic to others. By selectively targeting activation of the crosslinking agent to the sclera where it is not toxic, potential toxic effects in more susceptible tissues are avoided. That is, the crosslinking reagent is rendered effectively inactive by its caging with one or more blocking moieties. Upon light targeting the caging agent preferentially in a scleral tissue, the crosslinking reagent becomes uncaged and may crosslink with one or more molecules already present in the scleral tissue or co-introduced together with the crosslinking agent.

In specific embodiments, the crosslinking reagent is an individual molecule, although it may comprise a chain of crosslinking reagents that "depolymerizes," thereby allowing release of multiple crosslinking reagents for crosslinking with a scleral molecule, such as collagen.

Crosslinking reagents may be caged using a number of strategies. Caging may be accomplished by treating the native, uncaged molecule with a reactive precursor to a caging group. For example, the sidechain of the amino acid cysteine may be caged with the photo-removable o-nitrobenzyl group by treating a cysteine-containing protein with o-nitrobenzylbromide. Alternative strategies for caging proteins include chemical synthesis of the protein using solid-phase peptide synthesis starting with the appropriate caged amino acids, by direct translational incorporation into proteins using methods based on nonsense suppression, or by supplementing auxotrophic strains of bacteria with the caged amino acids.

In a specific embodiment, a crosslinking reagent is caged to render it inactive, prior to localization to the sclera, and it is activated upon exposure to an energy source. In a specific embodiment, the crosslinking reagent comprises a protein having amino acid side chains. Those amenable to modification with a protecting group, such as a photo-removable protecting groups, include cysteine, aspartate, glutamate, histidine, lysine, asparagine, glutamine, arginine, serine, threonine, or tyrosine, for example. Examples of photo-removable protecting groups includes o-nitrobenzyl, desyl, phenacyl, trans-o-cinnamoyl, coumarinyl, quinoline-2-onyl, xanthenyl, thioxanthenyl, selenoxanthenyl and anthracenyl, stilbenyl, and/or derivatives thereof. These protecting groups are added to the side chains as described elsewhere herein.

Thus, the crosslinking reagents of the present invention may comprise at least one amino acid residue and are in an inactive form by caging, wherein at least one amino acid sidechain, such as from cysteine, aspartate, glutamate, histidine, lysine, asparagine, glutamine, arginine, serine, threonine, tyrosine, or a combination thereof, comprises a photo-removable protecting group, such as at least one coumarinyl, quinoline-2-onyl, xanthenyl, thioxanthenyl, selenoxanthenyl and anthracenyl, and/or stilbenyl group, for example. In another embodiment, the crosslinking reagent is inactivated through caging in an ultrasound contrast agent, such as microbubbles or liposomes.

The molecule may be formulated so as to provide an effective concentration in the desired tissue. Although in some embodiments the molecule accumulates in non-affected tissue, this is not problematic for the individual, since precise targeting of the activating energy source to the sclera renders selective activation on or within the sclera. Other regions where the caged molecules accumulate are not treated with the activating energy; therefore, the caged molecules remain inactive and are eliminated via the kidneys and/or liver, for example. In a specific embodiment, the caged molecule is not harmful or toxic in any manner and is nevertheless excreted from the body, preferably less than about 48 hours after administration, and more preferably less than about 24 hours after administration.

In some embodiments, the molecule is coupled to a specific binding ligand that may bind to a specific target molecule within the sclera. The target molecule may be endogenous to the sclera, or it may be selectively delivered to the sclera by crosslinking the target molecule using two photon excitation. In these embodiments, the molecule will be delivered in higher concentrations to the target tissue. In a specific embodiment, various protein-binding domains such as leucine zipper domains are associated with the molecule.

V. Photopolymerization Embodiments

The present invention utilizes a molecule for administration to the sclera, in specific embodiments to strengthen at least part of the scleral tissue and/or increase the modulus of the sclera, and in particular embodiments these physiological alterations result in treatment and/or prevention of myopia in at least one eye of an individual. That is, in particular embodiments, a photopolymerizable molecule is employed to achieve such an effect. The photopolymerizable compound may be of any suitable kind, so long as it increases the modulus of the sclera and/or increases the strength of the sclera, for example, or so long as at least one symptom of myopia is ameliorated at least in part. The molecule preferably alters the physical and/or chemical properties of the tissue.

In particular aspects of the invention, a mixture of a monomer that is capable of being polymerized and a photoinitiator are provided to a sclera in an individual in need thereof. The molecule may be considered inactive, and in a particular context of the invention is in a non-polymerizable form, until light targets the molecule. Thus, upon administration of the molecule to the individual and its activation upon exposure to an energy source, the molecule becomes polymerized, thereby increasing the modulus and/or strengthening the sclera. In particular embodiments, the polymerization occurs among the monomers and/or with one or more molecules in the scleral tissue, such as collagen, for example. In other particular embodiments, the polymerization comprises polymerization of a monomer around a scleral molecule, such as collagen, glycosaminoglycans, proteoglycans, hyaluronan, dermatan and chondroitin sulphate-based proteoglycans, and the small proteoglycans, decorin and biglycan, for example.

Figure 10:
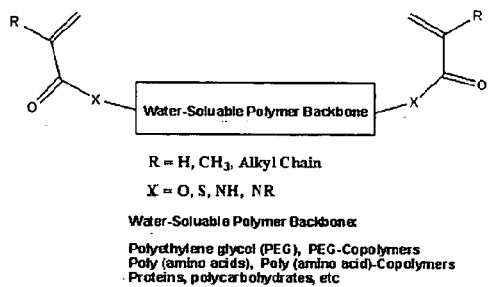
FIGS. 10A-10E illustrate some exemplary polymerizable water-soluble monomers (FIG. 10A) and water-soluble photoinitiators (FIGS. 10B-10E).
Figure 10:
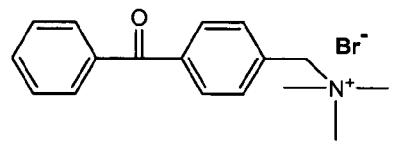
Figure 10:
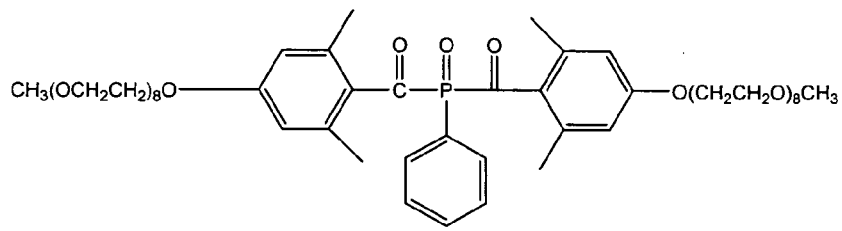
Figure 10:
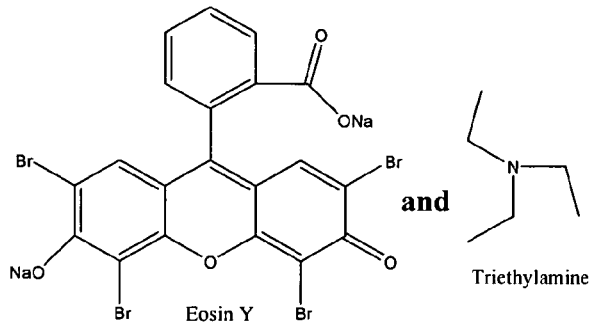
Figure 10:
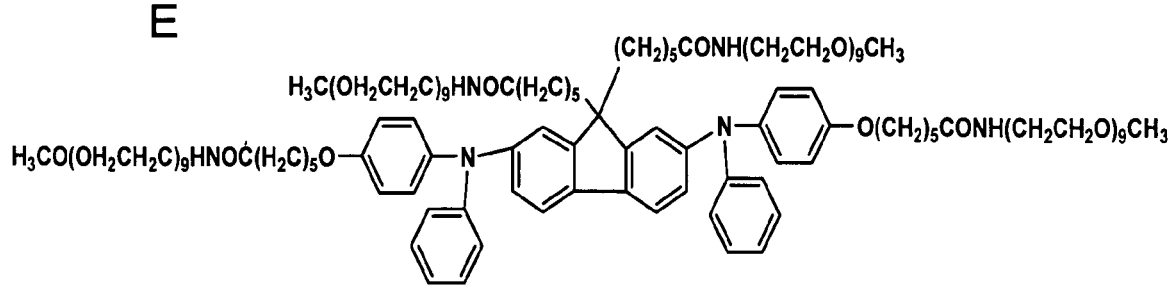

The photopolymerizable compounds may be defined as comprising one or more moieties, such as end groups, for example, at which polymerization occurs, either through polymerization with other monomers or polymer chains, through polymerization with itself, through polymerization with at least one molecule in the scleral tissue, or through polymerization with two or more of these embodiments. Non-limiting examples of polymerizable water-soluble monomers are provided in FIG. 10A.

In particular embodiments, the photopolymerizable compound comprises a polypeptide, such as natural elastin, engineered elastin, or a mixture thereof, for example. The engineered elastin may be produced in any suitable manner, although in specific embodiments one or more amino acids of elastin are altered upon exposure to a chemical or by site-directed mutagenesis of a polynucleotide that encodes elastin, for example. Chemical mutagenesis of a nucleic acid may be achieved by exposure to Benzo[a]pyrene, N-acetoxy-2-acetyl aminofluorene or aflotoxin B1, for example. Site-directed mutagenesis is well known in the art and also addressed in U.S. Pat. Nos. 5,220,007; 5,284,760; 5,354,670; 5,366,878; 5,389,514; 5,635,377; and 5,789,166, for example.

The engineered elastin, for example, can be modified by attachment of two or more methacryl or acryl groups. The elastin may be utilized as the monomer for photopolymerization, in specific embodiments. A skilled artisan recognizes that modified elastin is long-lived and chemically versatile.

Examples of polypeptides encompass amino molecule sequences comprising at least one of the 20 common amino acids in naturally synthesized proteins and/or at least one modified or unusual amino acid, including but not limited to 4-aminobutyric acid and those shown on Table 1 below.

TABLE 1

Modified and Unusual Amino Acids

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |

TABLE 1-continued

Modified and Unusual Amino Acids

| Abbr. | Amino Acid |
|---|---|
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Figure 11:
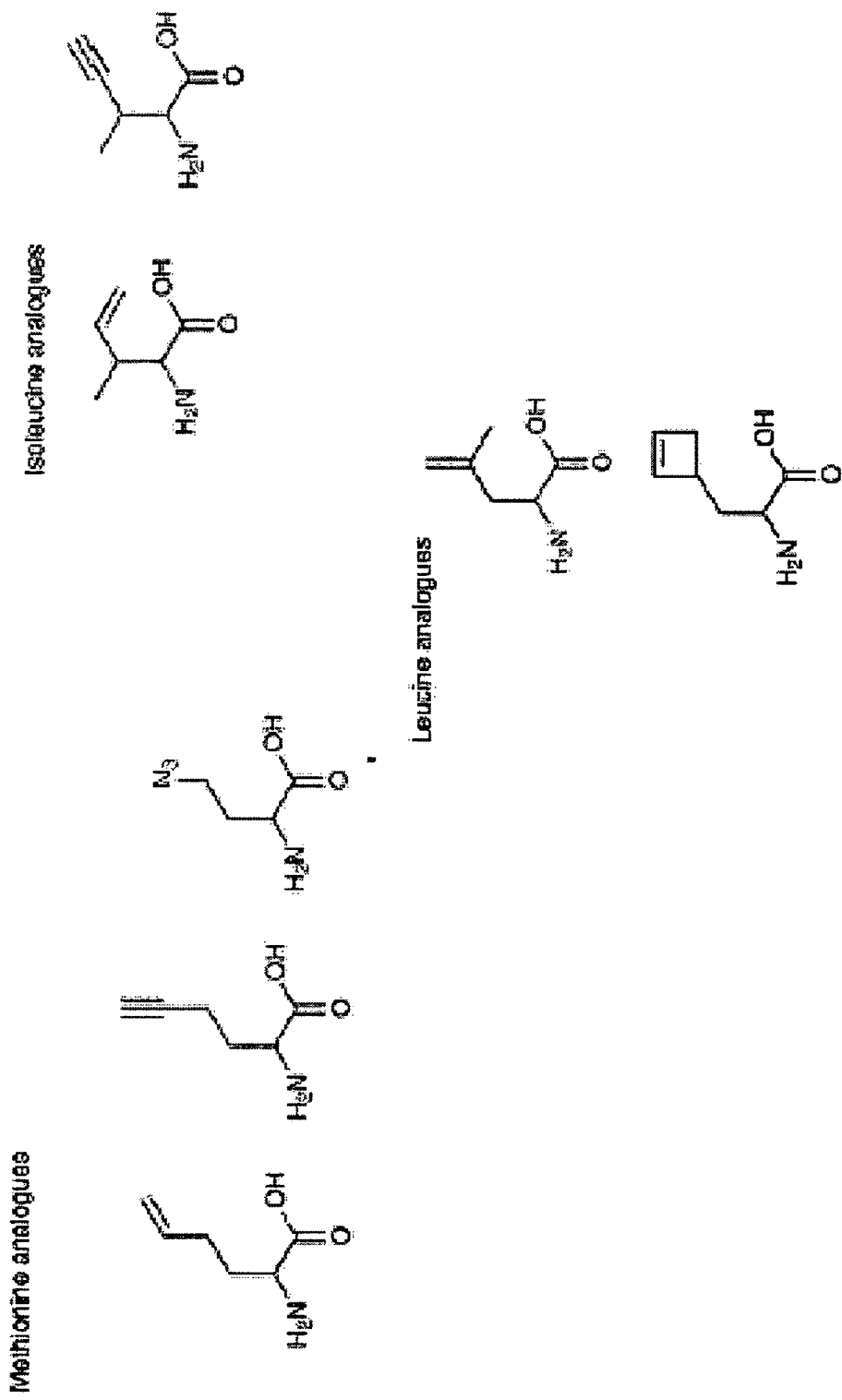
FIG. 11 shows exemplary analogs of methionine, isoleucine, and leucine for use as non-natural amino acids in embodiments of the invention.

Exemplary phenylalanine and tyrosine analogs include p-aminophenylalanine, p-ethynylphenylalanine, azidophenylalanine, O-acetyltyrosine, O-allyltyrosine, p-bromophenylalanine, m-iodo- and m-chlorotyrosine. Exemplary analogs of methionine, isoleucine, and leucine are provided in FIG. 11.

The photopolymerizable compound is preferentially provided with a photoinitiator. The photoinitiator is preferably water soluble and correlates to the light source that will be employed. In specific embodiments, the photoinitiator is inhibited by oxygen, thereby rendering it particularly well suited for avoiding strengthening of tissues that would find the strengthening deleterious, such as the walls of blood vessels. Examples of photoinitiators include those provided in FIGS. 10B-10E, including water-soluble photoinitiators that are single photon polymerization initiators or two photon polymerization initiators. Single photon initiators include phenylacetophenone derivatives ($\lambda$>320 nm), acyphosphineoxide derivatives ($\lambda$>385 nm), and quinone/amine mixtures ($\lambda$, 420 nm to 500 nm), for example. Two photon polymerization initiators include fluorene-based photoinitiators, for example.

VI. Formulations

The molecules of the present invention are formulated so as to provide an effective concentration in the desired tissue. Although in some embodiments the molecule accumulates in non-affected tissue, this is not problematic for the individual, since precise targeting of the activation energy source to the sclera renders selective activation within this tissue. Other regions where the molecules accumulate are not treated with the activating energy; therefore, the molecules remain inactive and are eliminated via the kidneys and/or liver. In some embodiments, the tissue-altering molecule is coupled to a specific binding ligand that may bind to a specific surface component of the target sclera or, if desired, by formulation with a carrier that delivers higher concentrations to the target tissue. In a specific embodiment, various protein binding domains such as leucine zipper domains are associated with the molecules of the invention.

The nature of the formulation will depend in part on the mode of administration and on the nature of the selected molecule. Any pharmaceutically acceptable excipient, or combination thereof, appropriate to the particular compound may be used. Thus, the compound may be administered as an aqueous composition, as a topical composition, as a transmucosal or transdermal composition, in an oral formulation or intravenous formulation, in a local injection (such as periocular or intraocular) or a combination thereof. The formulation may also include delivery vehicles, such as liposomes, for example.

VII. Administration and Dosage

Although the molecules of the invention can be administered in any of a wide variety of ways, including systemically, in particular embodiments it is administered locally (such as direct topical application to sclera, periocular injection, or retrobulbar injection for example).

The dose of tissue-altering molecule can vary widely depending on the mode of administration; the formulation in which it is carried, such as in the form of liposomes; or whether it is coupled to a target-specific ligand, such as an antibody or an immunologically active fragment. As is generally recognized, there is a nexus between the type of molecule, the formulation, the mode of administration, and the dosage level. Adjustment of these parameters to fit a particular combination is possible and routine.

VIII. Energy Source

The energy source comprises any stimulus that respectively uncages a caged crosslinking reagent or photopolymerizes a photopolymerizable compound. Although energy sources are well known in the art, exemplary forms of energy sources include light or ultrasound. In specific embodiments, single photon photochemistry, two photon photochemistry, or multi-photon photochemistry is utilized. In a specific embodiment, monochromatic light is utilized.

The various parameters used for effective, selective photoactivation of the molecules in the invention may be interrelated. Therefore, the dose should also be adjusted with respect to other parameters, for example, fluence, irradiance, duration of treatment, and time interval between administration of the dose and the therapeutic irradiation. All of these parameters should be adjusted to produce enhancement of visual function without significant damage to the ocular tissue, and a skilled artisan is well aware how to do so.

Compositions and methods related to two-photon absorption, for example, are well known in the art, although exemplary methods are described in U.S. Pat. No. 6,267,913, U.S. Pat. No. 6,472,541, and WO 00/31588, which are all incorporated by reference herein in their entirety.

IX. Assays for Therapeutic Effects

In a particular aspect of the invention, the sclera is strengthened by methods and compositions of the present invention. In an alternative description of the invention, the modulus of an ocular tissue is increased, thinning of the sclera is at least retarded, compliance is decreased, creep is decreased, and so forth. These parameters may be measured by suitable methods in the art before and/or after the methods of the present invention are employed, and these methods may be a qualitative assay or a quantitative assay.

The proposed treatment for myopia results in prevention or inhibition of development of myopia in non-myopic patients, in particular embodiments. In myopic patients the treatment should halt or slow the progression of the disease. Evaluation of the treatment effectiveness in clinical practice can be done using accepted diagnostic techniques such as ultrasound, optical coherence tomography, magnetic resonance imaging, fundus photography, scanning laser ophthalmology, slit lamp ophthalmology, etc. (Goss 1997, Haigis 2000). These techniques can be used to make measurements of ocular characteristics, for example, axial length, vitreous chamber length, and globe shape.

In vitro studies to evaluate the effectiveness of the treatment can be used to study the changes in the physical properties of the tissue, for example, permeability and mechanical characteristics. Quantization of the permeability may be done using methods such as MRI or particle detection in combination with Ussing chamber experiments (Olsen 1995). Expected changes in mechanical characteristics may include, but not be limited to or necessarily include, increased shear modulus, increased Young's modulus, increased compression modulus, decreased compliance, and decreased creep. Common biomechanical and rheological procedures may be used to quantify such treatment effects (Downs 2003, Jin 2001, Knapp 1997, McBrien 2003, St. Helen 1961, Examples 1 and 2 herein).

Other embodiments for measuring strength and modulus include ultrasound and wave propagation in the sclera.

EXAMPLES

The following examples are offered by way of example, and are not intended to limit the scope of the invention in any manner.

Example 1

Increasing Sclera Modulus by Poly(ethylene-glycol) Dimethacrylate (PEGDM) Treatment The present invention includes a method for treatment of myopia by altering the physical or chemical properties of the sclera. In one example of such treatment, photopolymerizable molecules may be used to obtain the desired results, including thickening, reinforcing, crosslinking, and strengthening of the sclera. Such molecules will be inactive upon administration and only activated by locally directed energy, like light or ultrasound. The application of said treatment will be in a pharmacologically approved method, preferably retrobulbar administration.

As a specific example, the inactive molecules can be applied retrobulbarly and given 5 to 60 minutes to diffuse into the sclera to the desired depth. Molecular perfusion may be monitored with fluorescent tags either attached to the inactive molecule or unattached but diffusing at the same rate as the molecules. The molecules can then be activated by irradiation with energy, for example UV light, for the proper dosage time (1 to 30 min.) to obtain desired results. The irradiation time for desired results can be adjusted based on the patient need, chosen molecules, diffusion time, light source, and delivery method. Future examinations can be used to determine if further treatment is necessary.

As a specific example of molecules that may be used, a mixture of poly(ethylene-glycol) dimethacrylate (PEGDM) with a photoinitiator ([(4-benzoylbenzyl)trimethylammonium bromide]) was chosen as a demonstration material. PEGDM is one suitable material for this treatment because of its ability to be polymerized, its water solubility, and its biocompatibility (Riley, 2001). A desirable photoinitiator should be water soluble like Compound 15, but the activation wavelength, the activation efficiency, the free radical production, and the toxicity are variables that may be adjusted to achieve the desired treatment results. The energy source provides a method of locally activating the treatment and in this example UV is used at levels similar to what has been used for in vivo studies on the cornea (Wollensak, 2003). The clinical light source will preferably be long wavelength (>400 nm) and multi-photon, for greater depth penetration, less cell toxicity, and more precise three dimensional localization of the treatment.

This example demonstrates the ability of such a treatment to increase the modulus of sclera and therefore strengthen the tissue. Studies were employed to determine the following: 1) if the shear modulus of sclera could be increased by perfusion with, and photopolymerization of, poly(ethylene-glycol) dimethacrylate (PEGDM) with a photoinitiator, 2) if the modulus was dependent on concentration of PEGDM, and 3) if the reaction was affected by oxygen concentration in the tissue.

Methods

Fresh 8 mm diameter scleral tissue sections were cut from the posterior pole of porcine eyes (<36 hrs post mortem) using an 8 mm trephine punch. Tissue sections were placed in Dulbecco's phosphate buffered saline (DPBS) for 24 hours at 22° C. prior to initial measurements of the storage modulus G', a measure of the elastic properties of the sample. G' was measured by oscillatory shear tests on a TA Instruments AR2000 rheometer fitted with a novel cleat tool (parallel walled square cleats 450 um sides, 600 um long, 1350 um center to center distance on a square lattice; Nickerson and Kornfield, 2005) that reduces wall slip, common in biological samples. The normal force during sample loading was ~0.1N. After loading, the tissue was equilibrated for 2 minutes in a 37° C. solution bath of DPBS. The tests were run at a constant amplitude stress (5 Pa) and angular frequency (1 rad/sec) for a period of 1 min. The scleral sections were then removed from the rheometer and placed in solutions of varying percent (0-25% w/w) 550 MW poly(ethylene-glycol) dimethacrylate (PEGDM) with 1% w/w of the exemplary photoinitiator [(4-benzoylbenzyl)trimethylammonium bromide]. The tissue was soaked in solution for 1 hour, taken out of solution and padded dry with a Kimwipe, and then placed in one of three environments as follows: 1) against a glass window in a sealed chamber the size of the tissue; 2) in an air purged atmosphere; or 3) in an argon-purged atmosphere. After 5 minutes with no irradiation, the sclera was exposed to 365 nm UV irradiation (5.0-~5.5 mW/cm2) for 30 min using a mercury lamp. After irradiation and photopolymerization, the scleral sections were placed in a DPBS rinse for 24 hours at 22° C. The final modulus was then measured using the same procedure as for the initial modulus.

Results

Figure 4:
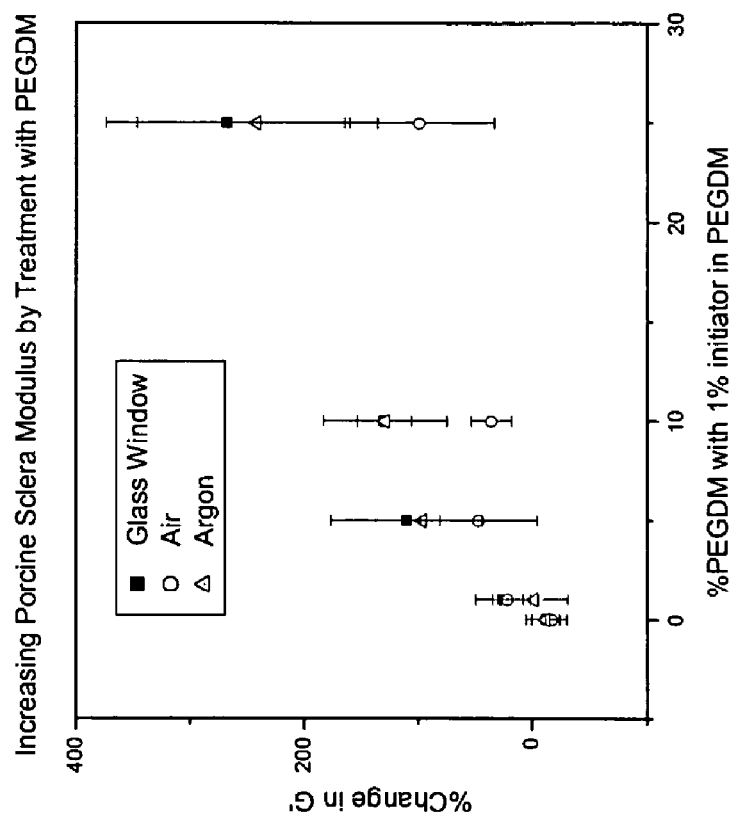
FIG. 4 shows an increase in porcine sclera modulus by treatment with poly(ethylene-glycol) dimethacrylate (PEGDM).

Each data point in FIG. 4 represents results from 4 tissue sections (AVG±SD). With a 25% PEGDM solution, larger changes in modulus occur in the argon environment than in the air environment (241±105% increase and 99±65% increase, respectively); while the small glass chamber allows changes (267±107%) close to that of argon. Less change results from lower concentration PEGDM solutions.

Clearly, the storage modulus of the sclera can be increased by treatment with photocrosslinkable monomers such as PEGDM. These experiments confirm both an oxygen dependence of the photopolymerization and a dose dependence of the modulus. Oxygen dependence is expected due to the tendency of oxygen to act as a free radical scavenger, and controlling the oxygen concentration in the tissue may provide a useful method of regulating the reaction. In addition, vasculature in the area may be less susceptible to polymerization and remain unchanged while the surrounding tissue is treated. The concentration-dependent modulus is expected because less support to the existing network is added at lower concentrations. This permits tuning of the mechanical properties of sclera based on solution dosage, in specific embodiments. The glass window isolates the tissue and as the number of radical scavengers is depleted, the reaction proceeds unhindered, as it would in argon. This method provides the additional benefit of sealing the tissue to prevent dehydration throughout the study.

Example 2

Increase of Scleral Structural Integrity

As described in Example 1, treatment for myopia may possibly utilize molecules such as PEGDM. In addition to variables described above, different molecular weight monomers may give rise to different properties, such as thickness, strength, flexibility, and permeability, in the treated tissue.

Studies were employed to determine if human sclera perfused with PEGDM solutions and irradiated with UV light would gain increased structural integrity as measured in the storage modulus G'.

Methods

Fresh 8 mm diameter scleral tissue sections were cut from the posterior pole of human donor eyes (<72 hrs p.m.) using an 8 mm trephine punch. Tissue sections were placed in Dulbecco's phosphate buffered saline (DPBS) for 24 hours at 5° C. prior to initial measurements of the storage modulus G', a measure of the elastic properties of the sample. G' was measured by oscillatory shear tests on a TA Instruments AR2000 rheometer fitted with a novel cleat tool (parallel walled square cleats 450 um sides, 600 um long, 1350 um center to center distance on a square lattice; Nickerson and Kornfield, 2005) which reduces wall slip, common in biological samples. The normal force during sample loading was ~0.1N. After loading, the tissue was equilibrated for 2 minutes in a 37° C. solution bath of DPBS. The tests were run at a constant amplitude stress (5 Pa) and angular frequency (1 rad/sec) for a period of 1 min. The scleral sections were then placed in solutions of varying percent (0, 10, 50% w/w) and molecular weight (550 or 875 MW) poly(ethylene-glycol) dimethacrylate (PEGDM) with 1% w/w photoinitiator ([(4-benzoylbenzyl)trimethylammonium bromide]). The tissue was soaked in solution for 1 hour, taken out of solution and padded dry with a Kimwipe, and then placed against a glass window in a sealed chamber the size of the tissue. The sclera was exposed to 365 nm UV irradiation (~4 mW/cm$^2$) for 30 min using a mercury lamp. After irradiation and photopolymerization, the scleral sections were placed in a DPBS rinse for 4.5 hours at 22° C. The final modulus was then measured using the same procedure as for the initial modulus.

Figure 5:
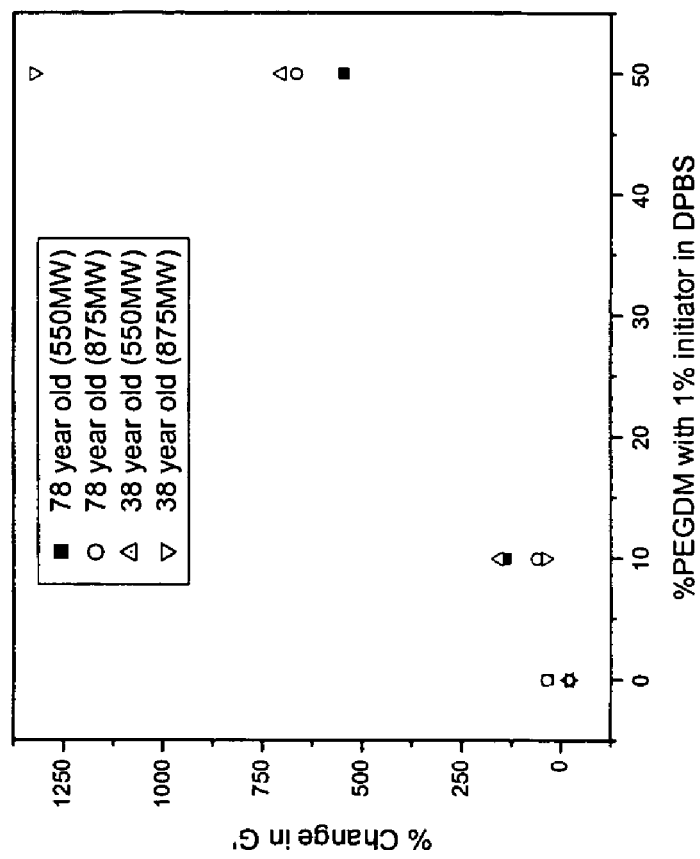
FIG. 5 illustrates an increase in human scleral modulus by treatment with PEGDM.

As seen in FIG. 5, the change in modulus increases with increased PEGDM concentration. From this data, no molecular weight dependence of modulus can be determined.

Human sclera can be strengthened by treatment with PEGDM solutions, and the results indicate that the modulus can be expected to have dose-dependent behavior. Although further study may be utilized to determine molecular weight dependence of the modulus, in specific embodiments of the invention, molecular weight of monomers in the solution influence directly or indirectly the final physical properties of the treated tissue.

Example 3

Exemplary Polymerization Initiators and Synthesis Thereof

Figure 6:
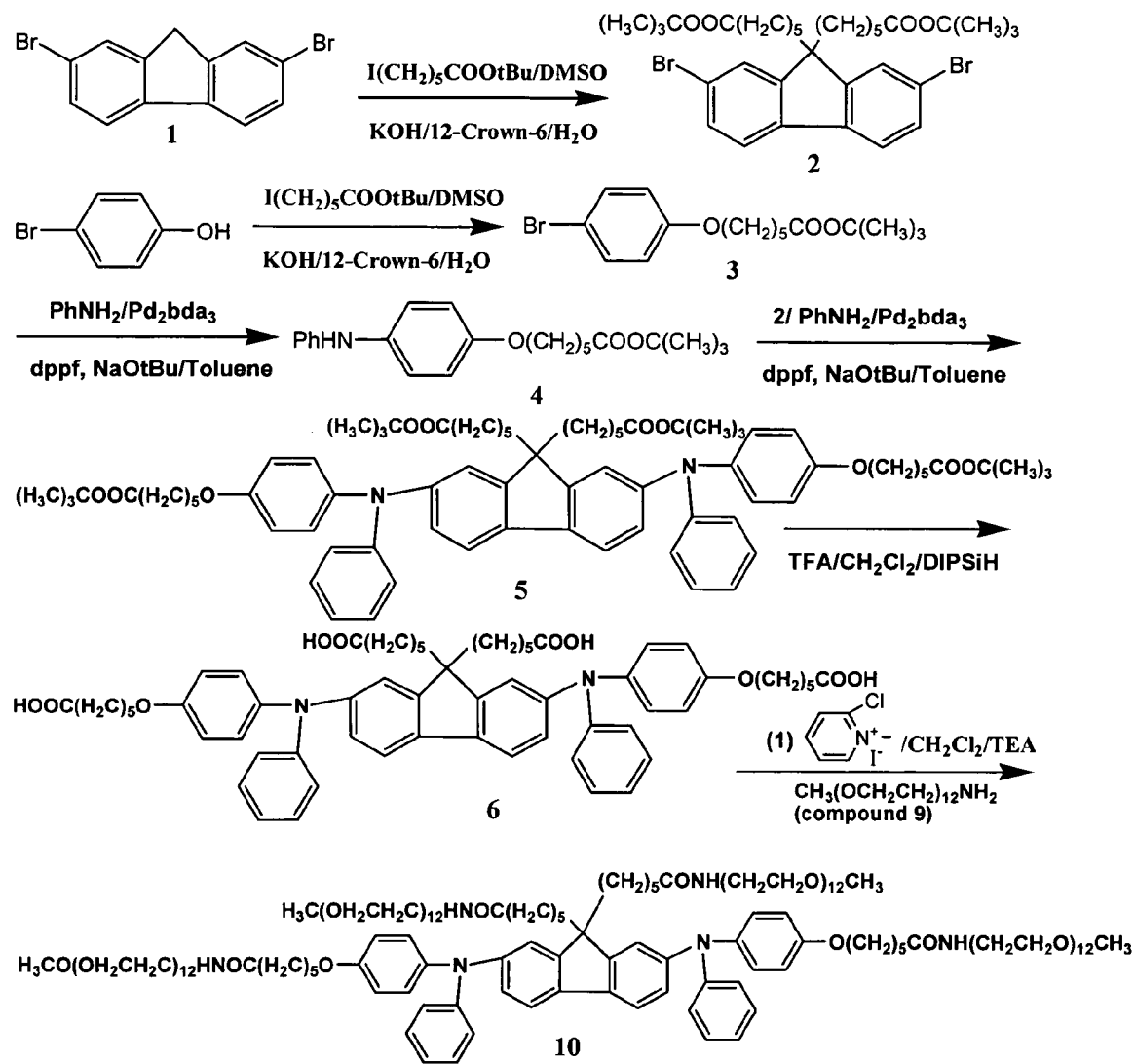
FIG. 6 provides an exemplary synthesis of two-photon polymerization initiators.

In embodiments wherein a photopolymerizable compound is employed, the compound is preferentially provided with a photoinitiator. Although a variety of photoinitiators may be utilized, FIG. 6 illustrates the synthesis of three exemplary polymerization initiators:

(1) Two-Photon Polymerization Initiator

Synthesis of Compound 2: To a flask were added 2.5 gm (7.71 mmol) of 2,7-dibromofluorene (compound 1), 4.8 gm (19.1 mmol) of tert-butyl 6-iodohexanoate and 200 mg of 12-crown-6 was added 80 mL of DMSO and 7 mL of water, followed by adding 1.5 gm (26.8 mmol) of KOH. The reaction mixture was stirred under Argon overnight. The reaction mixture was diluted by adding 500 mL of ethyl acetate and 400 mL of the brine solution. After shaking well, the organic layer was separated and washed again with the brine. The organic layer was dried over sodium sulfate and concentrated. Silica gel (150 gm) was loaded with hexane, the crude product in small amount of $CH_2Cl_2$ was loaded and the column was eluted with 0-70% $CH_2Cl_2$/hexane, the fractions were identified by TLC ($CH_2Cl_2$:Hexane=7:3) and the desired fractions were pooled and concentrated to give 4.5 g (84.7%) of the compound 2.

Synthesis of Compound 3: To a flask were added 2.0 gm (11.8 mmol) of 4-bromophenol, 2.7 gm (10.8 mmol) of tert-butyl 6-iodohexanoate and 100 mg of 12-crown-6 was added 40 mL of DMSO and 5 mL of water, followed by adding 1.0 gm (17.8 mmol) of KOH. The reaction mixture was stirred under Argon overnight. The reaction mixture was diluted by adding 200 mL of ethyl acetate and 200 mL of the brine solution. After shaking well, the organic layer was separated and washed again with the brine. The organic layer was dried over sodium sulfate and concentrated. Silica gel (100 gm) was loaded with hexane, the crude product in small amount of $CH_2Cl_2$ was loaded and the column was eluted with 0-50% $CH_2Cl_2$/hexane, the fractions were identified by TLC ($CH_2Cl_2$:Hexane=1:1), visualized by UV light and CAM stains, and the desired fractions were pooled and concentrated to give 3.1 g (76.5%) of the compound 3.

Synthesis of Compound 4: To a 50 mL-Shlenk tube were added 1.5 gm (4.3 mmol) of compound 3, 0.65 g (7.0 mmol) of aniline, 75 mg (0.082 mmol) of Pd2(dba)3 [Tris(dibenzylideneacetone)dipalladium (0)] and 95 mg (0.17 mmol) of DPPF [1,1'-Bis(diphenylphosphino)ferrocene] and 30 mL of toluene. The reaction mixture was stirred under argon for 20 min and was heated to 110° C., 600 mg (6.2 mmol) of sodium tert-butoxide was immediately added. The reaction mixture was sealed and heated at 110° C. for 30 min. After cooling, the mixture was poured out of the Shlenk tube into 200 mL of ethyl acetate, and the solution was washed twice with the brine, dried over sodium sulfate and concentrated. Silica gel (100 gm) was loaded with hexane, the crude product in small amount of $CH_2Cl_2$ was loaded and the column was eluted with 0-10% ethyl acetate/hexane, the fractions were identified by TLC (EtOAc:Hexane=1:9), visualized by UV light, and the desired fractions were pooled and concentrated to give 1.2 g (78.5%) of the compound 4.

Synthesis of Compound 5: To a 50 mL-Shlenk tube were added 0.88 gm (1.28 mmol) of compound 2, 1.0 g (2.81 mmol) of compound 4, 80 mg (0.087 mmol) of Pd2(dba)3 and 100 mg (0.18 mmol) of DPPF and 20 mL of toluene. The reaction mixture was stirred under argon for 20 min and was heated to 110° C., 670 mg (7.0 mmol) of sodium tert-butoxide was immediately added. The reaction mixture was sealed and heated at 110° C. for 2 h. After cooling, the mixture was poured out of the Shlenk tube into 200 mL of ethyl acetate, and the solution was washed twice with the brine, dried over sodium sulfate and concentrated. Silica gel (100 gm) was loaded with $CH_2Cl_2$, the crude product in small amount of $CH_2Cl_2$ was loaded and the column was eluted with 2×250 mL of $CH_2Cl_2$ and 2×250 of 5% ethyl acetate/$CH_2Cl_2$, the fractions were identified by TLC (EtOAc:$CH_2Cl_2$=5:95), visualized by UV light, and the desired fractions were pooled and concentrated to give 0.7 g (45.1%) of the compound 5.

Synthesis of Compound 5: To 0.30 gm (0.24 mmol) of compound 5 was added a solution of 20 mL of TFA (trifluoroacetic acid)/20 mL of $CH_2Cl_2$ containing 0.1 mL of triisopropylsilane. The reaction mixture was stirred under Argon for 2 h and the resulting mixture was diluted by adding 40 mL of toluene. The solvent was removed and the residue was co-evaporated three times with toluene. The crude product, compound 5, will be used without further purifications.

Figure 7:
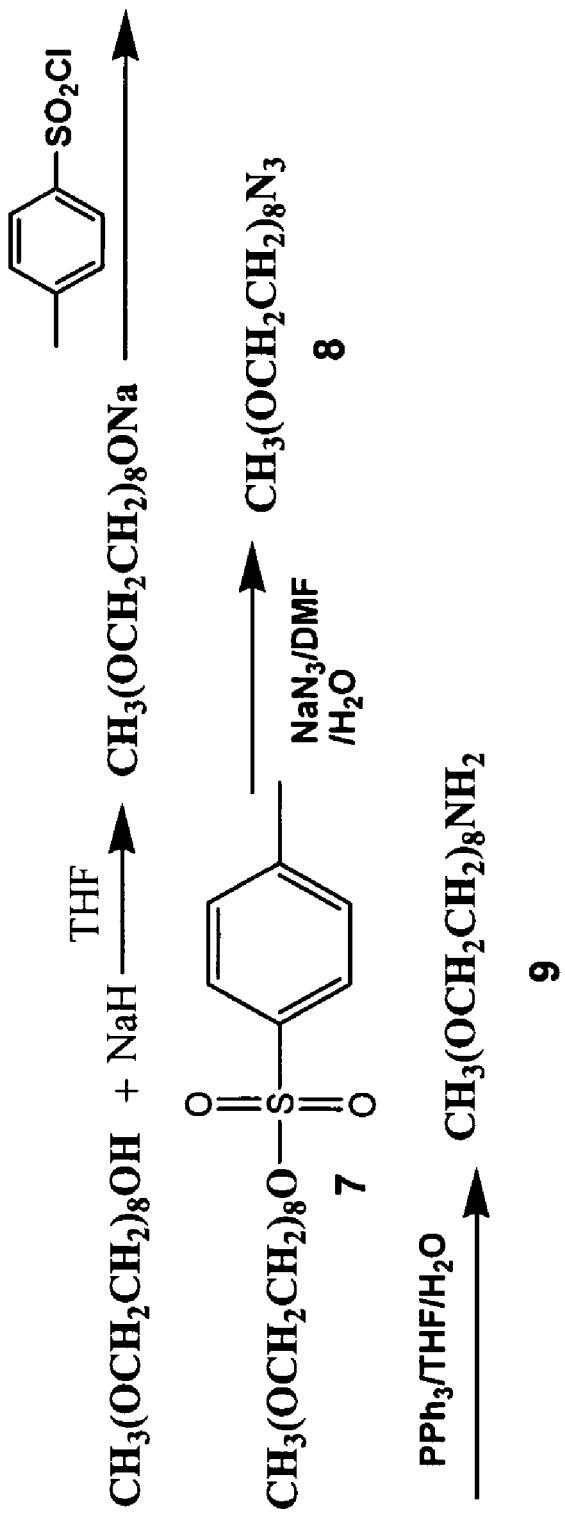
FIG. 7 illustrates an exemplary synthesis of ethylene glycol oligomers.

FIG. 7 illustrates an exemplary synthesis route of ethylene glycol oligomers.

Synthesis of Compound 7: To 5.0 gm (14.3 mmol) of poly(ethylene glycol) methyl ether (typical Mn 350) was added 50 mL of dry THF, while the solution was cooled into an ice-water bath, 0.68 gm (17.0 mmol) of NaH in mineral oil was added portion by portion. The reaction mixture was gradually warmed to room temperature within 2 h while stirring. The resulting mixture was recooled into the same ice-water bath, 4.1 gm (21.5 mmol) of toluene sulfonyl chloride was added and the mixture was stirred overnight. The solvent was removed and the residue was diluted by adding 150 mL of dichloromethane and 100 mL of brine, after shaking well, the organic layer was separated and washed one more time with the brine, dried over sodium sulfate and concentrated. Silica gel (100 gm) was loaded with $CH_2Cl_2$, the crude product in small amount of $CH_2Cl_2$ was loaded and the column was eluted with 1-5% $CH_3OH$/$CH_2Cl_2$, the fractions were identified by TLC ($CH_3OH$:$CH_2Cl_2$=8:92), visualized by Iodine, and the desired fractions were pooled and concentrated to give 7.4 g (82.8%) of the compound 7.

Synthesis of Compound 8: To 3.5 gm (5.59 mmol) of compound 7 was added 30 mL of DMF and 18 mL of water and 8.0 gm (123 mmol) of $NaN_3$. The resulting suspension was heated at 58° C. under Argon overnight. After removal of solvent, the residue was dissolved in 150 mL of dichloromethane and 100 mL of the brine. Organic layer was separated, dried over sodium sulfate and concentrated. Silica gel (100 gm) was loaded with $CH_2Cl_2$, the crude product in small amount of $CH_2Cl_2$ was loaded and the column was eluted with 1-5% $CH_3OH$/$CH_2Cl_2$, the fractions were identified by TLC ($CH_3OH$:$CH_2Cl_2$=5:95), visualized by Iodine, and the desired fractions were pooled and concentrated to give 2.4 g (86.4%) of the compound 8.

Synthesis of Compound 9: To 2.4 gm (4.82 mmol) of compound 8 was added 80 mL of THF, 1.8 mL of water and 12.5 gm (47.7 mmol) of triphenylphosphine. The reaction mixture was stirred under Argon overnight. After removing solvent, the residue was dissolved into 40 mL of 4% citric acid solution and 100 mL of ethyl acetate. Organic layer was separated and back extracted with 10 mL of 4% citric acid solution. The combined aqueous solution is extracted once with 20 mL of ethyl acetate. pH of the aqueous solution was adjusted to 14 by adding 5N NaOH solution. The resulting basic solution was extracted twice with dichloromethane (2×150 mL). The combined extracts were dried over sodium sulfate and concentrated to 1.7 gm (92.0%) of the pure compound 9.

Synthesis of Compound 10: To 100 mg (0.082 mmol) of compound 6 was added 252 mg (0.66 mmol) of compound 9, 200 mg (0.78 mmol) of 2-chloro-1-methylpyridium iodide, 1.0 mL of TEA (triethylamine) and 25 mL of dichloromethane. The reaction mixture was stirred overnight under Argon. The reaction mixture was diluted by adding 50 mL of dichloromethane, the reaction mixture was washed once with 1.0 N NaOH solution, once with 4% citric acid solution and once with the brine, dried over sodium sulfate and concentrated. Silica gel (50 gm) was loaded with $CH_2Cl_2$, the crude product in small amount of $CH_2Cl_2$ was loaded and the column was eluted with 1-8% $CH_3OH/CH_2Cl_2$, the fractions were identified by TLC ($CH_3OH:CH_2Cl_2=5:95$), visualized by long wavelength UV and the desired fractions were pooled and concentrated to give 220 mg 84.6%) of the compound 10.

Figure 8:
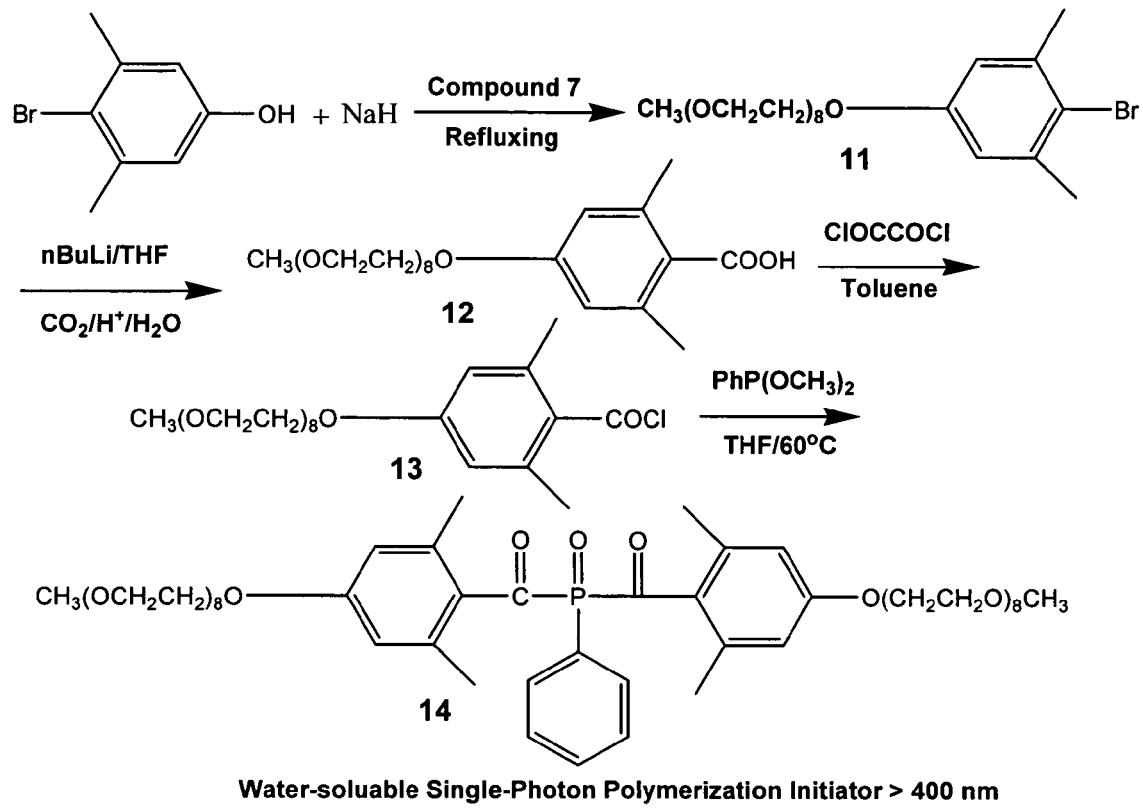
FIG. 8 provides an exemplary synthesis of single photon polymerization intiators.

(2) Single Photon Polymerization Initiators (i) Long Wavelength Single-Photon Polymerization Initiator FIG. 8 illustrates an exemplary synthesis route of a single photon polymerization initiator.

Synthesis of Compound 11: To a flask were added 4.0 gm (20 mmol) of 4-bromo-3,5-dimethylphenol, was added 50 mL of dry THF, while the solution was cooled into an ice-water bath, 0.90 gm (22.5 mmol) of NaH in mineral oil was added portion by portion. The reaction mixture was gradually warmed to room temperature within 2 h while stirring. The resulting mixture was recooled into the same ice-water bath, 8.0 gm (12.8 mmol) of compound 7 and 1.0 gm of 18-crown-6 were added and the mixture was refluxed overnight under Argon. The solvent was removed and the residue was diluted by adding 150 mL of dichloromethane and 100 mL of brine, after shaking well, the organic layer was separated and washed one more time with the brine, dried over sodium sulfate and concentrated. Silica gel (100 gm) was loaded with $CH_2Cl_2$, the crude product in small amount of $CH_2Cl_2$ was loaded and the column was eluted with 1-5% $CH_3OH/CH_2Cl_2$, the fractions were identified by TLC ($CH_3OH:CH_2Cl_2=8:92$), visualized by Iodine, and the desired fractions were pooled and concentrated to give 7.1 g (93.1%) of the compound 11.

Synthesis of Compound 12: To 2.5 gm of compound 11 was added 40 mL of dry THF. While the resulting solution was cooled into a dry ice-acetone bath (−78° C.), 3.5 mL (9.8 mmol) of 2.8 M nBuLi in hexane was added slowly. The reaction mixture was gradually warmed to room temperature and re-cooled into the same dry ice-acetone bath, and $CO_2$ gas was bubbled into this solution for 30 min. The reaction mixture was stirred overnight. After adding 20 mL of 1.0 N HCl solution was added, the mixture was concentrated, the residue was dissolved in 200 mL of dichloromethane. The organic layer was washed twice with 4% citric acid solution (2×100 mL). Silica gel (70 gm) was loaded with $CH_2Cl_2$, the crude product in small amount of $CH_2Cl_2$ was loaded and the column was eluted with 1-8% $CH_3OH/CH_2Cl_2$, the fractions were identified by TLC ($CH_3OH:CH_2Cl_2=8:92$), visualized by Iodine, and the desired fractions were pooled and concentrated to give 0.9 g (44.5%) of the compound 12.

(ii) Short Wavelength Single-Photon Polymerization Initiator

Figure 9:
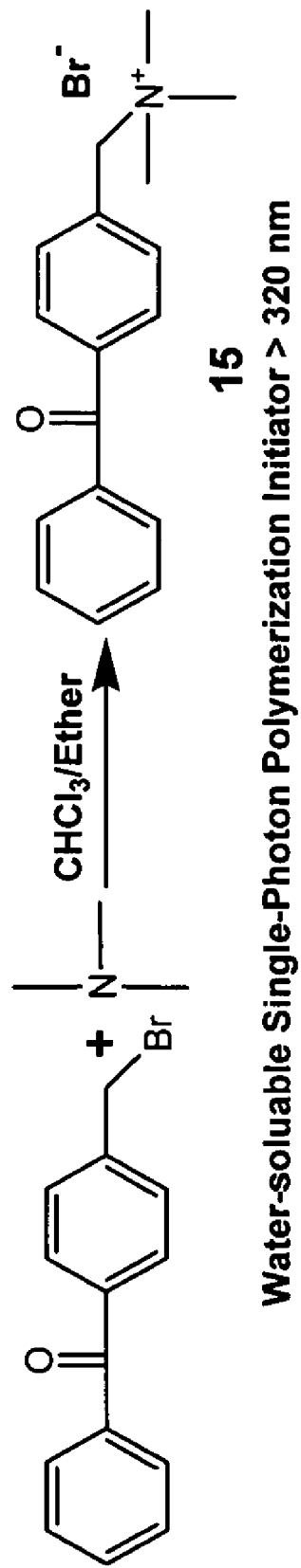
FIG. 9 illustrates a short wavelength single photon polymerization initiator.

FIG. 9 illustrates an exemplary synthesis route of short wavelength single photon polymerization initiator.

Synthesis of Compound 15: To 0.5 gm (1.88 mmol) of 4-(bromomethyl)benzophenone were added 15 mL of chloroform, 15 mL of ether and 2.2 mL of trimethylamine. The reaction mixture was stirred for 3 h, solvent was removed. The residue was dissolved in 15 mL of methanol and 80 mL of ether was added. The mixture was cooled at −20° C. for 3 h, the white precipitate formed and filtered. After drying over a high vacuum, 0.55 gm (90.4%) of the desired product, compound 15, was obtained.

Example 4

Treatment of Myopia

In a particular embodiment of the present invention, a patient with progressive high myopia receives retrobulbar injection of a compound of the present invention, such as monomers of poly(ethylene-glycol) dimethacrylate, and then after about 15-120 minutes undergoes 2 photon irradiation of sclera in the posterior pole region. Following polymerization of the PEGDM, the scleral modulus is increased and myopic progression is prevented or retarded. Treatment is repeated, such as at about 2-12 months later, for example, while the eye is followed for axial enlargement using, for example, partial coherence interferometry.

In another embodiment of the present invention, there is a method of identifying a tissue to be treated based on the intrinsic light scattering from targeted tissue such as sclera. Optical coherence tomography (OCT) with visible or infrared light is used to detect alterations in the physical or chemical nature of sclera in the eye. OCT can be used to see not only the structure in the eye but also the mobility of the structures by Doppler OCT and the chemical nature, in some embodiments. In this embodiment, the OCT and/or its variants are used to determine the nature of the sclera with altered properties to permit guided treatment. Treatment could be the photo-uncaging or photo-activation of administered agents in or near the sclera.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference herein.

Patents

U.S. Pat. No. 5,220,007
U.S. Pat. No. 5,284,760
U.S. Pat. No. 5,354,670
U.S. Pat. No. 5,366,878
U.S. Pat. No. 5,389,514;
U.S. Pat. No. 5,635,377
U.S. Pat. No. 5,789,166
U.S. Pat. No. 5,756,541
U.S. Pat. No. 5,798,349
U.S. Pat. No. 5,910,510
U.S. Pat. No. 5,935,942
U.S. Pat. No. 6,128,525
U.S. Pat. No. 6,140,314
U.S. Pat. No. 6,225,303
U.S. Pat. No. 6,248,727
U.S. Pat. No. 6,267,913
U.S. Pat. No. 6,472,541
WO 00/31588

Publications

Downs, J. C., et al., Viscoelastic Characterization of Peripapillary Sclera: Material Properties by Quadrant in Rabbit and Monkey Eyes, Journal of Biomechanical Engineering, February 2003, Vol 125, 124-131.

Goss, D. A., et al., OPTOMETRIC CLINICAL PRACTICE GUIDELINE CARE OF THE PATIENT WITH MYOPIA Reference Guide for Clinicians, American Optometric Association 1997.

Haigis, W., et al., Comparison of immersion ultrasound biometry and partial coherence interferometry for intraocular lens calculation according to Haigis, Graefe's Arch Clin Exp Ophthalmol 2000, 238:765-773.

Jin, M., Grodzinsky, A., Effect of Electrostatic Interactions between Glycosaminoglycans on the Shear Stiffness of Cartilage: A Molecular Model and Experiments, Macromolecules 2001, 34: 8330-8339.

Knapp, D. M., et al., Rheology of reconstituted type I collagen gel in confined compression, J. Rheol. 41 (5), September/October 1997.

McBrien, N. A., Gentle, A., Role of the sclera in development and pathological complications of myopia, Progress in Retinal and Eye Research, 2003, 22: 307-338.

Olsen, T. W., et al., Human Scleral Permeability Effects of Age, Cryotherapy, Transscleral Diode Laser, and Surgical Thinning, Investigative Ophthalmology & Visual Science, August 1995, Vol 36, No. 9, 1893-1903.

Riley, S. L., et al. Formulation of PEG-based hydrogels affects tissue-engineered cartilage construct characteristics. Journal of Materials Science: Materials in Medicine. 2001; 12:983-990.

St. Helen, R., McEwen, W. K., Rheology of the Human Sclera 1. Anelastic Behavior, Am J Ophthalmol. 1961 October, 52:539-48.

Wollensak, G., Spoerl, E., Seiler, T. Riboflavin/ultraviolet-A-induced crosslinking for the treatment of keratoconus. Am. J. Ophthalmol. 2003; 135: 620-627.

We claim:

1. A method of treating axial myopia in an individual in need thereof, comprising administering to the sclera of the individual a photopolymerizable compound selected from the group consisting of polyethylene glycol (PEG), a protein, or a polysaccharide; and a photo initiator, and exposing light on the photopolymerizable compound to form a covalent bond with another molecule of the compound, with a molecule of the sclera, or with both.

2. The method of claim 1, wherein the polyethylene glycol (PEG) further comprises a moiety selected from the group consisting of an acrylate, diacrylate, triacrylate, methacrylate, dimethacrylate, trimethacrylate, or vinyl group.

3. The method of claim 1, wherein the polysaccharide comprises poly(hyaluronic acid), dermatansulfate, chondroitinsulfate or keratansulfate.

4. The method of claim 1, wherein the protein is elastin.

5. The method of claim 4, wherein the elastin is native elastin or an engineered elastin.

6. The method of claim 5, wherein the engineered elastin has therefor one or more natural amino acid substitutions suitable for polymerization.

7. The method of claim 5, wherein the engineered elastin has therefore one or more non-natural amino acids comprising one or more chemical groups that are appropriate for polymerization, for photoinitiation, or both.

8. The method of claim 1, wherein the exposure to light is directed to a region of the sclera identified by diagnostic imaging.

9. The method of claim 1, wherein the exposure to light is directed to a region of the sclera identified by ultrasound imaging, OCT imaging, OCT Doppler imaging, or magnetic resonance imaging (MRI).

10. The method of claim 1, wherein the compound is administered to the sclera by retrobulbar injection.

* * * * *